US011600121B2

(12) United States Patent
Ehlert et al.

(10) Patent No.: US 11,600,121 B2
(45) Date of Patent: Mar. 7, 2023

(54) SYSTEMS AND METHODS FOR CONDITIONAL REMOTE UNLOCKING OF IDENTIFIED CONTAINERS

(71) Applicant: UnitedHealth Group Incorporated, Minnetonka, MN (US)

(72) Inventors: Jennie Audrey Ehlert, Wayzata, MN (US); Andrew Tsong-Bo Cheng, Golden Valley, MN (US); Emre Charles Adabag, Minneapolis, MN (US); Samantha Roberta Detor, Wayzata, MN (US); Steven J. Catani, Athens, GA (US)

(73) Assignee: UnitedHealth Group Incorporated, Minnetonka, MN (US)

( * ) Notice: Subject to any disclaimer, the term of this patent is extended or adjusted under 35 U.S.C. 154(b) by 21 days.

(21) Appl. No.: 17/083,760

(22) Filed: Oct. 29, 2020

(65) Prior Publication Data
US 2022/0028193 A1 Jan. 27, 2022

Related U.S. Application Data

(60) Provisional application No. 63/054,276, filed on Jul. 21, 2020.

(51) Int. Cl.
*G07C 9/00* (2020.01)
*G16H 20/10* (2018.01)
(Continued)

(52) U.S. Cl.
CPC ......... *G07C 9/00309* (2013.01); *G06F 21/32* (2013.01); *G16H 10/60* (2018.01); *G16H 20/10* (2018.01)

(58) Field of Classification Search
CPC .... G07C 9/00309; G06F 21/32; G16H 10/60; G16H 20/10; G16H 40/67
See application file for complete search history.

(56) References Cited

U.S. PATENT DOCUMENTS

| 5,582,323 A | 12/1996 | Kurtenbach |
| 5,710,551 A | 1/1998 | Ridgeway |

(Continued)

FOREIGN PATENT DOCUMENTS

| WO | 2013/025520 A2 | 2/2013 |
| WO | 2016/196145 A1 | 12/2016 |
| WO | 2019/074469 A1 | 4/2019 |

OTHER PUBLICATIONS

Jain, Anmol et al. "Alerting System For Medicine Dispensing," International Journal of Advanced Research in Engineering and Technology (IJARET), vol. 10, Issue 2, Mar.-Apr. 2019, pp. 457-462.

(Continued)

*Primary Examiner* — Vernal U Brown
(74) *Attorney, Agent, or Firm* — Alston & Bird LLP

(57) ABSTRACT

Access to a container may be controlled by receiving a container identifier provided from a container identification module associated with the container; determining access criteria for the container; receiving a provider authorization signal generated based on user input received via a provider user interface; receiving biosensor signals generated by biosensors associated with a user; receiving historical access data associated with the user, wherein the historical access data indicates one or more objects historically accessed by user; determining whether the provider authorization signal, the one or more biosensor signals, and the historical access data satisfy the access criteria for the container; and upon determining the access criteria for the container are satisfied, (Continued)

generating a signal causing an unlocking mechanism to unlock the container.

21 Claims, 11 Drawing Sheets

(51) Int. Cl.
*G16H 10/60* (2018.01)
*G06F 21/32* (2013.01)

(56) References Cited

U.S. PATENT DOCUMENTS

| | | |
|---|---|---|
| 7,885,725 B2 | 2/2011 | Dunn |
| 8,108,068 B1 | 1/2012 | Boucher et al. |
| 8,193,918 B1 | 6/2012 | Shavelsky et al. |
| 8,397,310 B2 | 3/2013 | Parris et al. |
| 8,506,023 B2 | 8/2013 | Goldie |
| 8,626,531 B2 | 1/2014 | Williams et al. |
| 8,636,172 B2 | 1/2014 | Dunn |
| 8,744,620 B2 | 6/2014 | Shavelsky et al. |
| 8,797,138 B2 | 8/2014 | Myers et al. |
| 8,950,224 B2 | 2/2015 | Spencer |
| 9,211,233 B2 | 12/2015 | Shavelsky et al. |
| 9,400,873 B2 | 7/2016 | Kamen et al. |
| 9,593,523 B1 | 3/2017 | Trimble et al. |
| 9,600,634 B2 | 3/2017 | Bell et al. |
| 9,659,424 B2 | 5/2017 | Huber et al. |
| 9,836,897 B2 | 12/2017 | Briskey |
| 9,984,213 B2 | 5/2018 | Howieson et al. |
| 10,354,464 B2 | 7/2019 | Feltham et al. |
| 10,510,442 B2 | 12/2019 | Adams et al. |
| 2003/0174554 A1 | 9/2003 | Dunstone et al. |
| 2005/0168320 A1 | 8/2005 | Henderson et al. |
| 2008/0179387 A1 | 7/2008 | Cantlay et al. |
| 2009/0125324 A1 | 5/2009 | Keravich et al. |
| 2010/0100237 A1* | 4/2010 | Ratnakar ............... A61J 7/0418 221/97 |
| 2010/0176146 A1 | 7/2010 | Ben-Dor |
| 2013/0151267 A1 | 6/2013 | Mehdizadeh |
| 2015/0005934 A1 | 1/2015 | Bell et al. |
| 2015/0259110 A1 | 9/2015 | Blackbum |
| 2015/0272825 A1* | 10/2015 | Lim ....... G16H 40/67 340/5.2 |
| 2015/0278479 A1 | 10/2015 | Ervin |
| 2015/0327691 A1* | 11/2015 | Alshammari ............. A47F 1/04 312/7.2 |
| 2017/0010665 A1 | 1/2017 | Tanaka et al. |
| 2017/0061095 A1 | 3/2017 | Waskin et al. |
| 2017/0156985 A1 | 6/2017 | Guldan |
| 2018/0185245 A1* | 7/2018 | Poddar ................. A61J 7/0409 |
| 2019/0080792 A1 | 3/2019 | Chack et al. |
| 2019/0228669 A1 | 7/2019 | Baym et al. |
| 2019/0378602 A1 | 12/2019 | LaTorraca et al. |
| 2020/0038600 A1* | 2/2020 | Bitton ................... G16H 20/17 |

OTHER PUBLICATIONS

Shukur Mohammad Hussein. "Design a Mobile Medication Dispenser Based on IoT Technology," International Journal of Innovation Creativity and Change, vol. 6, Issue 2, (2019), pp. 242-250.

Yang, Geng et al. "A Health-IoT Platform Based on the Integration of Intelligent Packaging, Unobtrusive Bio-Sensor, and Intelligent Medicine Box," IEEE Transactions on Industrial Informatics, vol. 10, No. 4, Nov. 2014, pp. 2180-2191.

* cited by examiner

SYSTEMS AND METHODS FOR CONDITIONAL REMOTE UNLOCKING OF IDENTIFIED CONTAINERS

CROSS-REFERENCE TO RELATED APPLICATIONS

This patent application claims priority to U.S. Provisional Patent Appl. Ser. No. 63/054,276, filed Jul. 21, 2020, which is incorporated herein by reference in its entirety.

BACKGROUND

As remote healthcare services become more common, a persistent challenge faced by remote healthcare providers is providing medications, medical devices, diagnostic tests, and other medical supplies and treatment related items to patients. Those patients' homes generally lack access to such medical supplies and treatment related items, and therefore patients must still undertake inconvenient processes for obtaining these supplies, such as awaiting delivery of the supplies, visiting a supply location (e.g., a pharmacy), or relying solely on in-home medical care. However, existing supply chains for medical supplies are designed to limit access to medical supplies in certain instances, such as to limit the likelihood of misuse of those medical supplies. To avoid potentially harmful misuse of certain medical supplies (such as prescription medications), care providers (e.g., doctors) first assess the patient to determine medical needs of the patient and then the doctor provides access to only those medical supplies that would be helpful to the patient.

Thus, remote assessment and selective access to medical supplies are two challenges of providing remote healthcare. These challenges are not limited to prescription medications however, as remote patient assessments may be facilitated if specific diagnostic supplies were available to the patient only as allowed by a medical professional.

Accordingly, a need exists for systems and methods facilitating selective remote access to various objects, such as medical supplies.

BRIEF SUMMARY

Systems and methods discussed herein enable the unlocking of (and access to an interior of) containers through application of conditions and/or multiple signals providing data for assessing satisfaction of those conditions. For example, a signal may be provided from a physician-operated computing entity based on physician-provided user input indicating a type of drug or diagnostic that has been prescribed or is indicated for a patient. A second signal may be provided from a biosensor such as a thermometer or pulse oximeter associated with the patient. A third signal indicates a container's identity which, in turn, may be associated with its contents. A computer system determines what container identities are eligible to be opened using some combination of the first and second signals. If a particular container identifier is determined to be eligible, the system triggers an unlocking mechanism to open the container.

Certain embodiments are directed to a computer-implemented method of unlocking a container. In certain embodiments, the method comprises: receiving, via one or more processors, a container identifier provided from a container identification module associated with a locked container; determining, based at least in part on the container identifier, one or more access criteria for the locked container; receiving, via one or more processors, a provider authorization signal generated based at least in part on user input received via a provider user interface; receiving, via the one or more processors, one or more biosensor signals generated by one or more biosensors associated with a user; determining, via the one or more processors, whether one or more of the provider authorization signal and the one or more biosensor signals satisfy the one or more access criteria for the locked container; and upon determining the one or more access criteria for the locked container are satisfied, generating a signal causing an unlocking mechanism to unlock the locked container. In certain embodiments, the method further comprises receiving historical access data associated with the user, wherein the historical access data indicates one or more objects historically accessed in association with the user, and determinations of whether the access criteria are satisfied additionally comprise considerations of whether the historical access data satisfies the access criteria.

In various embodiments, generating a signal causing an unlocking mechanism to unlock the locked container comprises: transmitting a signal from the one or more processors to a cradle comprising an unlocking mechanism, wherein the locked container is associated with the cradle; and causing the unlocking mechanism of the cradle to unlock the locked container. Moreover, at least one access criterion of the one or more access criteria may comprise historical data of a first biosensor signal of the one or more biosensor signals satisfying one or more biosensor criteria. In certain embodiments, the one or more biosensor signals are generated by one of a temperature sensor or a blood oxygen sensor. In certain embodiments, the one or more biosensor signals comprise a first biosensor signal, and wherein the method further comprises: receiving a second biosensor signal generated by a second biosensor; and wherein at least one access criterion of the one or more access criteria comprise the second biosensor signal satisfying one or more biosensor criteria. In certain embodiments, generating a signal causing an unlocking mechanism to unlock the locked container comprises generating an electromagnetic field. In certain embodiments, the container identification module comprises at least one of: a radio-frequency identification (RFID) reader, an optical sensor, or a color sensor. In certain embodiments, the method further comprises: upon generating a signal causing an unlocking mechanism to unlock the locked container, determine whether one or more replenishment criteria are satisfied for one or more objects identified as associated with the container identifier, and upon determining that the one or more replenishment criteria are satisfied, initiate an order for a new container housing one or more replenishment objects.

Certain embodiments are directed to a system for unlocking a container. In various embodiments, the system comprises: one or more memory storage areas; and one or more processors collectively configured to: receive a container identifier provided from a container identification module associated with a locked container; determine, based at least in part on the container identifier, one or more access criteria for the locked container; receive a provider authorization signal generated based at least in part on user input received via a provider user interface; receive one or more biosensor signals generated by one or more biosensors associated with a user; determine whether one or more of the provider authorization signal and the one or more biosensor signals satisfy the one or more access criteria for the locked container; and upon determining the one or more access criteria for the locked container are satisfied, generate a signal causing an unlocking mechanism to unlock the locked container. In certain embodiments, the processors are further configured to receive historical access data associated with the user, wherein the historical access data indicates one or more objects historically accessed in association with the user, and determinations of whether the access criteria are satisfied additionally comprise considerations of whether the historical access data satisfies the access criteria.

In various embodiments, generating a signal causing an unlocking mechanism to unlock the locked container comprises: transmitting a signal from the one or more processors to a cradle comprising an unlocking mechanism, wherein the locked container is associated with the cradle; and causing the unlocking mechanism of the cradle to unlock the locked container. In certain embodiments, at least one access criterion of the one or more access criteria comprises historical data of a first biosensor signal of the one or more biosensor signals satisfying one or more biosensor criteria. In various embodiments, the one or more biosensor signals are generated by one of a temperature sensor or a blood oxygen sensor. Moreover, in certain embodiments the one or more biosensor signals comprise a first biosensor signal, and wherein the method further comprising: receiving a second biosensor signal generated by a second biosensor; and wherein at least one access criterion of the one or more access criteria comprise the second biosensor signal satisfying one or more biosensor criteria. In certain embodiments, generating a signal causing an unlocking mechanism to unlock the locked container comprises generating an electromagnetic field. Moreover, in various embodiments, the container identification module comprises at least one of: a radio-frequency identification (RFID) reader, an optical sensor, or a color sensor.

Certain embodiments are directed to a computer program product for unlocking a container, the computer program product comprising at least one non-transitory computer-readable storage medium having computer-readable program code portions stored therein. In various embodiments, the computer-readable program code portions are configured to: receive a container identifier provided from a container identification module associated with a locked container; determine based at least in part on the container identifier, one or more access criteria for the locked container; receive a provider authorization signal generated based at least in part on user input received via a provider user interface; receive one or more biosensor signals generated by one or more biosensors associated with a user; receive historical access data associated with the user, wherein the historical access data indicates one or more objects historically accessed in association with the user; determine whether one or more of the provider authorization signal and the one or more biosensor signals satisfy the one or more access criteria for the locked container; and upon determining the one or more access criteria for the locked container are satisfied, generate a signal causing an unlocking mechanism to unlock the locked container. Certain embodiments further comprise receiving historical access data associated with the user, wherein the historical access data indicates one or more objects historically accessed in association with the user, and determinations of whether the access criteria are satisfied additionally comprise considerations of whether the historical access data satisfies the access criteria.

In certain embodiments, generating a signal causing an unlocking mechanism to unlock the locked container comprises: transmitting a signal to a cradle comprising an unlocking mechanism, wherein the locked container is associated with the cradle; and causing the unlocking mechanism of the cradle to unlock the locked container. In certain embodiments, the one or more biosensor signals are generated by one of a temperature sensor or a blood oxygen sensor. In various embodiments, the one or more biosensor signals comprise a first biosensor signal, and wherein the method further comprising: receiving a second biosensor signal generated by a second biosensor; and wherein at least one access criterion of the one or more access criteria comprise the second biosensor signal satisfying one or more biosensor criteria.

Various embodiments are directed to a system for unlocking a container. In certain embodiments, the system comprises: a cradle configured to accept a container thereon, wherein the cradle comprises: a communication module configured to: receive container identification data from the container; receive biosensor signals from one or more biosensors; communicate data with a management computing entity; a processor configured to: determine access criteria for a container accepted on the cradle based at least in part on the container identification data and data received from the management computing entity; and based at least in part on the biosensor signals and data received from the management computing entity, generate an unlocking signal upon determining the access criteria are satisfied for the container; and an unlocking mechanism configured to, upon receipt of the unlocking signal from the processor, unlock the container accepted on a surface of the cradle.

In certain embodiments, the access criteria comprise a historical access criteria specifying a user accessed a separate container prior to gaining access to the container, and wherein historical access data is received from the management computing entity.

BRIEF DESCRIPTION OF THE SEVERAL VIEWS OF THE DRAWINGS

Reference will now be made to the accompanying drawings, which are not necessarily drawn to scale, and wherein.

DETAILED DESCRIPTION

Figure 1:
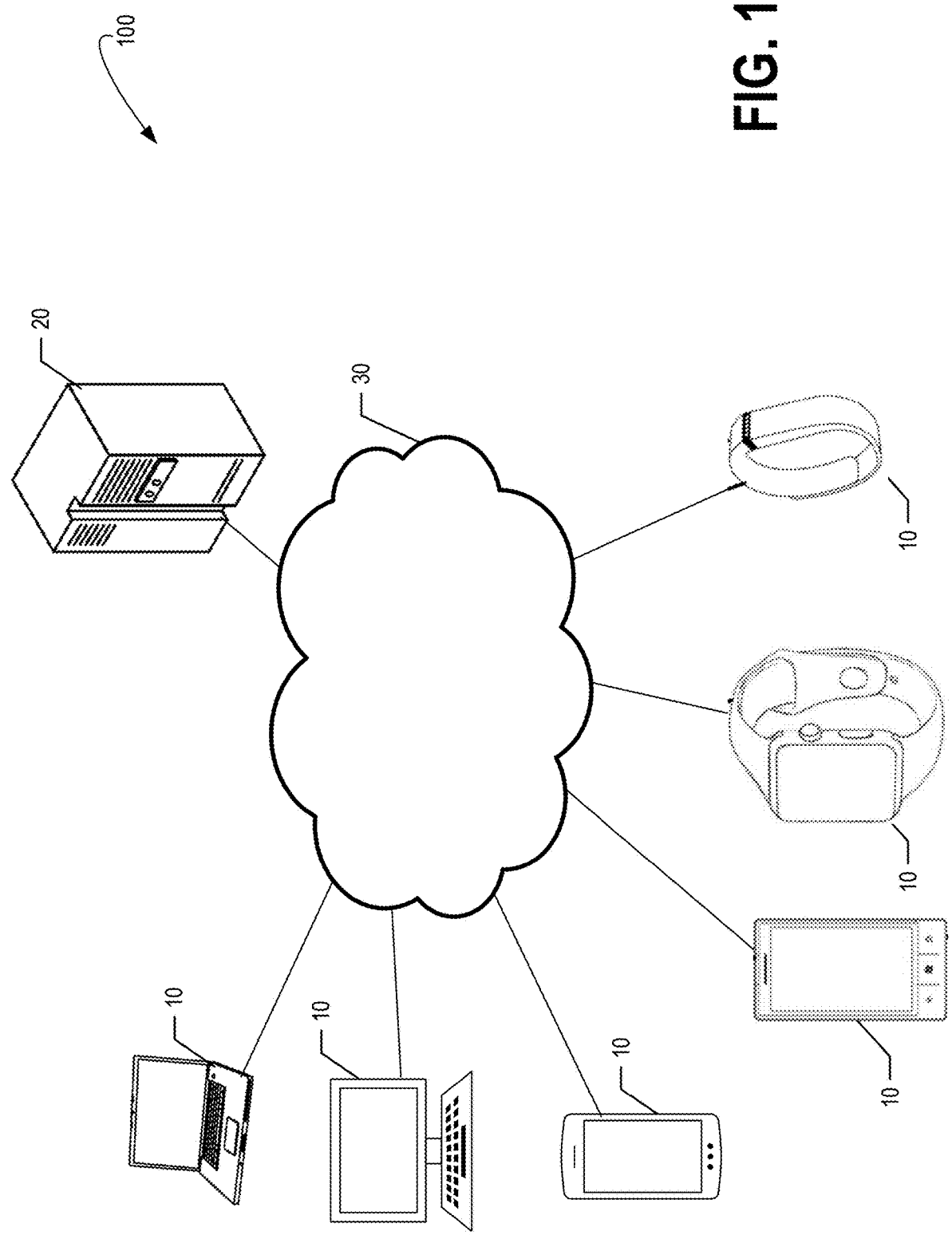
FIG. 1 is a diagram of a system that can be used in conjunction with various embodiments.

The present disclosure more fully describes various embodiments with reference to the accompanying drawings. It should be understood that some, but not all embodiments are shown and described herein. Indeed, the embodiments may take many different forms, and accordingly this disclosure should not be construed as limited to the embodiments set forth herein. Rather, these embodiments are provided so

I. Computer Program Products, Methods, and Computing Entities

Embodiments of the present invention may be implemented in various ways, including as computer program products that comprise articles of manufacture. Such computer program products may include one or more software components including, for example, software objects, methods, data structures, and/or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media.

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magneto resistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of a data structure, apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

II. Exemplary System Architecture

FIG. 1 provides an illustration of a platform 100 that can be used in conjunction with various embodiments of the present invention. As shown in FIG. 1, the platform 100 may comprise one or more user computing entities 10, one or more management computing entities 20, one or more networks 30, and/or the like. Each of the components of the system may be in electronic communication with, for example, one another over the same or different wireless or wired networks 30 including, for example, a wired or wireless Personal Area Network (PAN), Local Area Network (LAN), Metropolitan Area Network (MAN), Wide Area Network (WAN), and/or the like. Additionally, while FIG. 1 illustrates certain system devices as separate, standalone devices, the various embodiments are not limited to this particular architecture.

a. Exemplary Management Computing Entity

Figure 2:
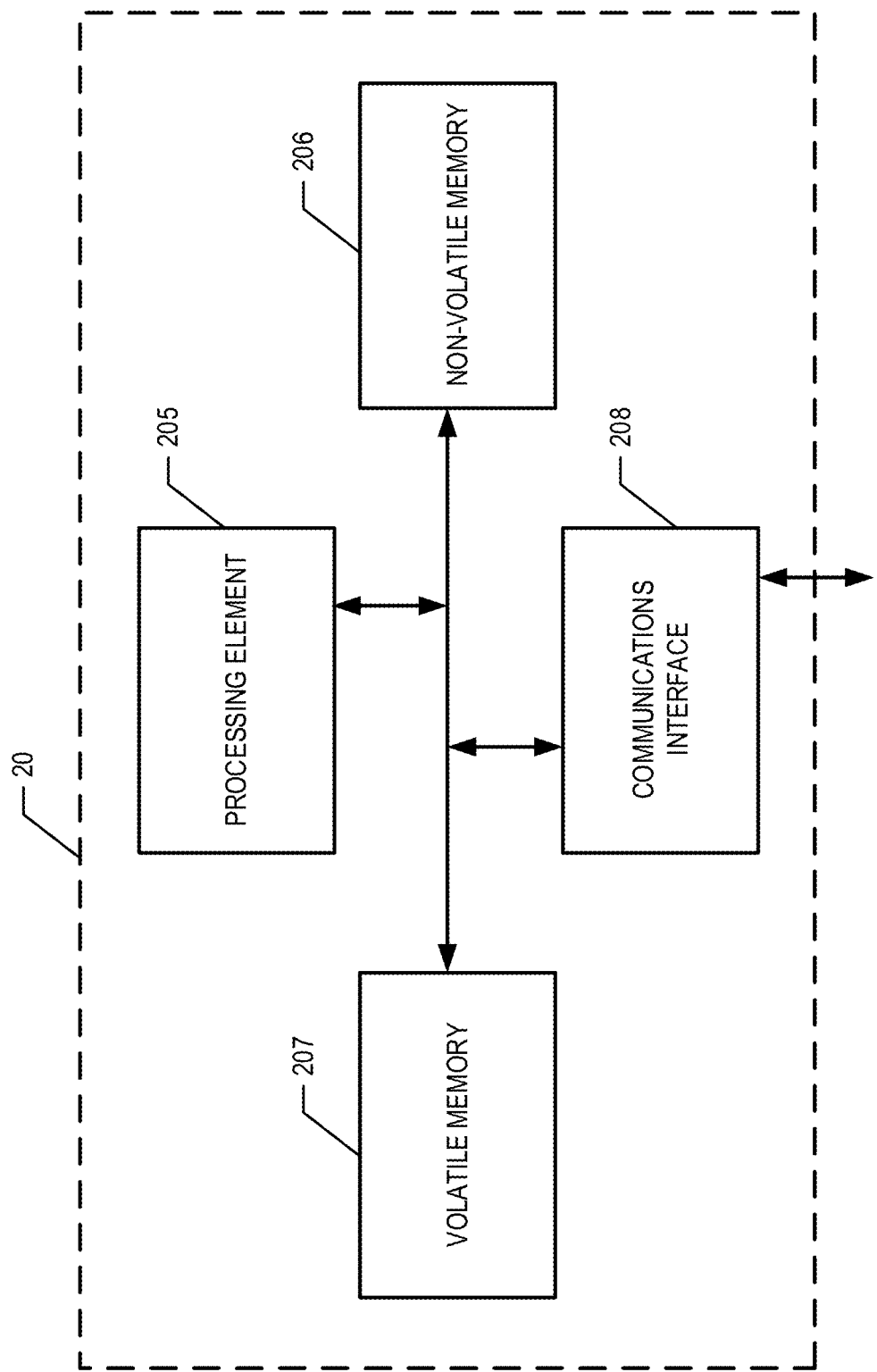
FIG. 2 is a schematic of a management computing entity in accordance with certain embodiments.

FIG. 2 provides a schematic of a management computing entity 20 according to one embodiment of the present invention. The management computing entity 20 of certain embodiments is configured to manage operation of a plurality of cradles 450 (and/or containers 410) discussed in greater detail herein, and to receive data from one or more additional data sources to facilitate management of operation of these cradles 450 and/or containers 410. In general, the terms computing device, entity, device, system, and/or similar words used herein interchangeably may refer to, for example, one or more computers, computing devices, computing entities, desktop computers, mobile phones, tablets, phablets, notebooks, laptops, distributed systems, terminals, servers or server networks, blades, gateways, switches, processing devices, set-top boxes, relays, routers, network access points, base stations, the like, and/or any combination of devices adapted to perform the functions, operations, and/or processes described herein. Such functions, operations, and/or processes may include, for example, transmitting, receiving, operating on, processing, displaying, storing, determining, generating/creating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the management computing entity 20 may also include one or more network and/or communications interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the management computing entity 20 may include or be in communication with one or more processing elements 205 (also referred to as processors, processing circuitry, and/or similar terms used herein interchangeably) that communicate with other elements within the management computing entity 20 via a bus, for example. As will be understood, the processing element 205 may be embodied in a number of different ways. For example, the processing element 205 may be embodied as one or more complex programmable logic devices (CPLDs), microprocessors, multi-core processors, coprocessing devices, application-specific instruction-set processors (ASIPs), and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the management computing entity 20 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 210 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or memory media may store databases, database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably may refer to a structured collection of records or information/data that is stored in a computer-readable storage medium, such as via a relational database, hierarchical database, and/or network database.

In one embodiment, the management computing entity 20 may further include or be in communication with volatile media (also referred to as volatile storage, memory, memory storage, memory circuitry and/or similar terms used herein interchangeably). In one embodiment, the volatile storage or memory may also include one or more volatile storage or memory media 215 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory media may be used to store at least portions of the databases, database instances, database management system entities, data, applications, programs, program modules, scripts, source code, object code, byte code, compiled code, interpreted code, machine code, executable instructions, and/or the like being executed by, for example, the processing element 205. Thus, the databases, database instances, database management system entities, data, applications, programs, program modules, scripts, source code, object code, byte code, compiled code, interpreted code, machine code, executable instructions, and/or the like may be used to control certain aspects of the operation of the management computing entity 20 with the assistance of the processing element 205 and the operating system.

As indicated, in one embodiment, the management computing entity 20 may also include one or more network and/or communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, management computing entity 20 may be configured to communicate via wireless external communication networks using any of a variety of protocols, such as general packet radio service (GPRS), Universal Mobile Telecommunications System (UMTS), Code Division Multiple Access 200 (CDMA200), CDMA200 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), IR protocols, NFC protocols, RFID protocols, IR protocols, ZigBee protocols, Z-Wave protocols, 6LoWPAN protocols, Wibree, Bluetooth protocols, wireless universal serial bus (USB) protocols, and/or any other wireless protocol. The management computing entity 20 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), HyperText Markup Language (HTML), and/or the like.

As will be appreciated, one or more of the management computing entity's components may be located remotely from other management computing entity 20 components, such as in a distributed system. Furthermore, one or more of the components may be aggregated and additional components performing functions described herein may be included in the management computing entity 20. Thus, the management computing entity 20 can be adapted to accommodate a variety of needs and circumstances, such as including various components described with regard to the mobile app 600 (executing on the user computing entity 10)—including various input/output interfaces.

b. Exemplary User Computing Entity

Figure 3:
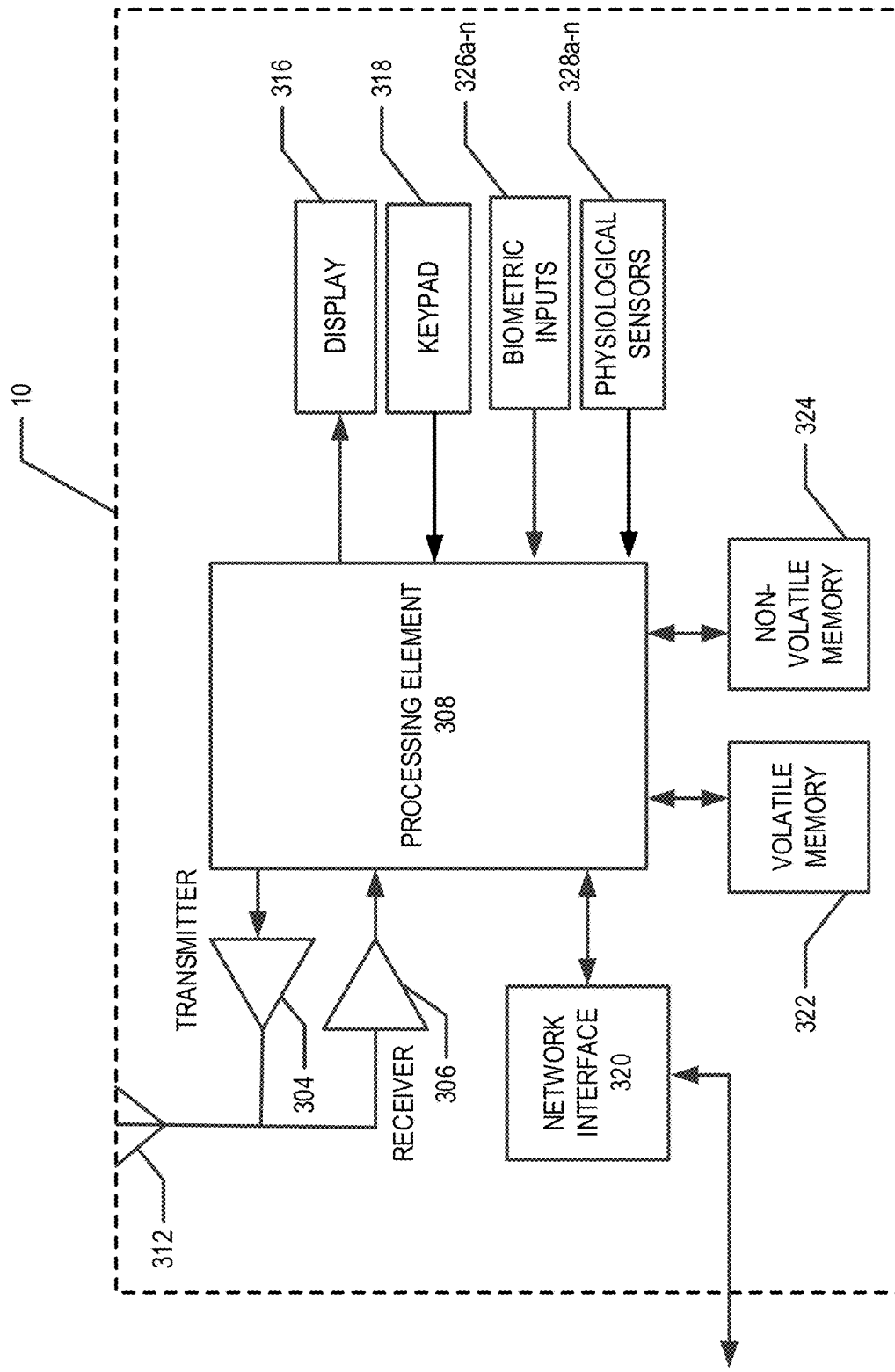
FIG. 3 is a schematic of a user computing entity in accordance with certain embodiments.

FIG. 3 provides an illustrative schematic representative of user computing entity 10 that can be used in conjunction with embodiments of the present invention. In various embodiments, the user computing entity 10 may comprise one or more mobile devices, wearable computing devices, and/or the like. As shown in FIG. 3, an user computing entity 10 can include an antenna 312, a transmitter 304 (e.g., radio), a receiver 306 (e.g., radio), and a processing element 308 that provides signals to and receives signals from the transmitter 304 and receiver 306, respectively. The signals provided to and received from the transmitter 304 and the receiver 306, respectively, may include signaling information/data in accordance with an air interface standard of applicable wireless systems to communicate with various devices, such as a management computing entity 20, another user computing entity 10, and/or the like. In an example embodiment, the transmitter 304 and/or receiver 306 are configured to communicate via one or more SRC protocols. For example, the transmitter 304 and/or receiver 306 may be configured to transmit and/or receive information/data, transmissions, and/or the like of at least one of Bluetooth protocols, low energy Bluetooth protocols, NFC protocols, RFID protocols, IR protocols, Wi-Fi protocols, ZigBee protocols, Z-Wave protocols, 6LoWPAN protocols, and/or other short range communication protocol. In various embodiments, the antenna 312, transmitter 304, and receiver 306 may be configured to communicate via one or more long range protocols, such as GPRS, UMTS, CDMA200, 1×RTT, WCDMA, GSM, EDGE, TD-SCDMA, LTE, E-UTRAN, EVDO, HSPA, HSDPA, Wi-Fi, Wi-Fi Direct, WiMAX, and/or the like. In this regard, the user computing entity 10 may be capable of operating with one or more air interface standards, communication protocols, modulation types, and access types. More particularly, the user computing entity 10 may operate in accordance with any of a number of wireless communication standards and protocols. In a particular embodiment, the user computing entity 10 may operate in accordance with multiple wireless communication standards and protocols, such as GPRS, UMTS, CDMA200, 1×RTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the user computing entity 10 can communicate with various other devices using concepts such as Unstructured Supplementary Service information/data (USSD), Short Message Service (SMS), Multimedia Messaging Service (MMS), Dual-Tone Multi-Frequency Signaling (DTMF), and/or Subscriber Identity Module Dialer (SIM dialer). The user computing entity 10 can also download changes, add-ons, and updates, for instance, to its firmware, software (e.g., including executable instructions, applications, program modules), and operating system.

According to one embodiment, the user computing entity 10 may include location determining aspects, devices, modules, functionalities, and/or similar words used herein interchangeably to acquire location information/data regularly, continuously, or in response to certain triggers. For example, the user computing entity 10 may include outdoor positioning aspects, such as a location module adapted to acquire, for example, latitude, longitude, altitude, geocode, course, direction, heading, speed, UTC, date, and/or various other information/data. In one embodiment, the location module can acquire information/data, sometimes known as ephemeris information/data, by identifying the number of satellites in view and the relative positions of those satellites. The satellites may be a variety of different satellites, including LEO satellite systems, DOD satellite systems, the European Union Galileo positioning systems, the Chinese Compass navigation systems, Indian Regional Navigational satellite systems, and/or the like. Alternatively, the location information/data may be determined by triangulating the authentication computing entity's 30 position in connection with a variety of other systems, including cellular towers, Wi-Fi access points, and/or the like. Similarly, the user computing entity 10 may include indoor positioning aspects, such as a location module adapted to acquire, for example, latitude, longitude, altitude, geocode, course, direction, heading, speed, time, date, and/or various other information/data. Some of the indoor aspects may use various position or location technologies including RFID tags, indoor beacons or transmitters, Wi-Fi access points, cellular towers, nearby computing entities (e.g., smartphones, laptops) and/or the like. For instance, such technologies may include iBeacons, Gimbal proximity beacons, BLE transmitters, NFC transmitters, and/or the like. These indoor positioning aspects can be used in a variety of settings to determine the location of someone or something to within inches or centimeters.

The user computing entity 10 may also comprise a user interface device comprising one or more user input/output interfaces (e.g., a display 316 and/or speaker/speaker driver coupled to a processing element 308 and a touch interface, keyboard, mouse, and/or microphone coupled to a processing element 308). For example, the user interface may be configured to provide an application (e.g., mobile app), browser, interactive user interface, dashboard, webpage, and/or similar words used herein interchangeably executing on and/or accessible via the user computing entity 10 to cause display or audible presentation of information/data and for user interaction therewith via one or more user input interfaces. In one embodiment, the functionality described herein (and user interface) may be provided as a standalone app executing on the user computing entity 10. In such an implementation, the mobile app 600 may be integrated with a variety of other apps executing on the user computing entity 10 to provide authentication functionality for other apps. Moreover, the user interface can comprise or be in communication with any of a number of devices allowing the user computing entity 10 to receive information/data, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the user computing entity 10 and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the user computing entity 10 can capture, collect, store information/data, user interaction/input, and/or the like.

In various example embodiments, the user computing entity 10 may comprise one or more biometric input components 326a-n (e.g., sensors, elements) for receiving or capturing biometric inputs or information/data (e.g., regularly, continuously, or in response to certain triggers). For example, the user computing entity 10 may comprise a touch sensitive region and/or display for capturing fingerprint scans, in an example embodiment. In another example, the user computing entity 10 may comprise cameras and/or image capturing devices for capturing images (e.g., image information/data) of an iris and/or face to determine blink rates or skin responses and/or detect coughing episodes. In another example, the user computing entity 10 may comprise microphones for capturing cough samples for cough detection and recognition. As should be understood, the user computing entity 10 may comprise various biometric input components 326a-n (e.g., sensors, elements) for receiving biometric input and information/data from a user. In various example embodiments, the user computing entity 10 can regularly, continuously, or in response to certain triggers capture such information/data (e.g., image information/data and/or biometric information/data).

In another example embodiment, the user computing entity 10 may comprise one or more physiological components 328a-n (e.g., sensors, elements) for capturing physiological inputs or information/data (e.g., regularly, continuously, or in response to certain triggers). For example, the user computing entity 10 may comprise microelectromechanical (MEMS) components, biological and chemical sensing components, electrocardiogram (ECG) components, electromyogram (EMG) components, electroencephalogram (EEG)-based neural sensing components, optical sensing components, electrical sensing components, sound components, vibration sensing components, and/or the like. Through such components various types of physiological information/data can be captured—such as heart rate information/data, oxygen saturation information/data, carbon dioxide information/data, temperature information/data, breath rate information/data, perspiration information/data, neural information/data, cardiovascular sounds information/data, pulmonary sounds information/data, and/or various other types of information/data. In yet other embodiments, the user computing entity 10 may be configured to receive biometric input data from external computing entities (e.g., external computing entities executing detailed biometric testing, such as blood analysis or other laboratory-based testing). It should be understood that such biometric data may be received from any of a variety of sources.

In another example embodiment, the user computing entity 10 may comprise one or more accelerometers, gyroscopes, and/or inertial measurement units (referred to herein separately and collectively as accelerometers 330) for capturing accelerometer information/data. For example, the accelerometers may capture static and dynamic acceleration, angular velocity, and degrees of freedom (DOF) to provide highly accurate orientation, position, and velocity information/data (e.g., accelerometer information/data).

The user computing entity 10 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, information/data, applications, programs, program modules, scripts, source code, object code, byte code, compiled code, interpreted code, machine code, executable instructions, and/or the like to implement the functions of the user computing entity 10.

c. Exemplary Networks

In one embodiment, any two or more of the illustrative components of the platform 100 of FIG. 1 may be configured to communicate with one another via one or more networks 30. The networks 30 may include, but are not limited to, any one or a combination of different types of suitable communications networks such as, for example, cable networks, public networks (e.g., the Internet), private networks (e.g., frame-relay networks), wireless networks, cellular networks, telephone networks (e.g., a public switched telephone network), or any other suitable private and/or public networks. Further, the networks 30 may have any suitable communication range associated therewith and may include, for example, global networks (e.g., the Internet), MANs, WANs, LANs, or PANs. In addition, the networks 30 may include any type of medium over which network traffic may be carried including, but not limited to, coaxial cable, twisted-pair wire, optical fiber, a hybrid fiber coaxial (HFC) medium, microwave terrestrial transceivers, radio frequency communication mediums, satellite communication mediums, or any combination thereof, as well as a variety of network devices and computing platforms provided by network providers or other entities.

III. Exemplary Container and Cradle

FIGS. 4-8 illustrate various views of an example secure supply system 400 for securely holding one or more objects (e.g., medical supplies, prescription medications, diagnostic systems/components, and/or the like) provided to an end user. As shown, the secure supply system 400 of the example embodiment comprises a lockable container 410 for securely holding the one or more objects and a cradle 450. In the illustrated example embodiment, the cradle 450 is configured to support the container 410 and to unlock a locked container upon satisfaction of one or more unlocking criteria (also referred to herein as access criteria). The illustrated cradle 450 comprises local processing resources, one or more communication transmitters and/or receivers, one or more unlocking components (e.g., electronic unlocking components, electromechanical unlocking components, and/or the like), one or more container identifier reading components (e.g., optical-based readers, radio-frequency identification readers, and/or the like), and/or the like. Because the cradle 450 comprises processing, communication, and appropriate unlock mechanisms, the container 410 need not include expensive powered components. Thus, in certain embodiments, the container 410 may be embodied as a low-cost disposable container 410. However it should be understood that in certain embodiments the container 410 may be reusable in certain embodiments (e.g., either with refill objects of the same object type (e.g., a container may be refilled with the same prescription medication) such that a container identifier associated with the container can remain unchanged, or with objects of a differing object type (such that a container identifier may be changed to reflect current contents of the container)).

a. Exemplary Container

Figure 4:
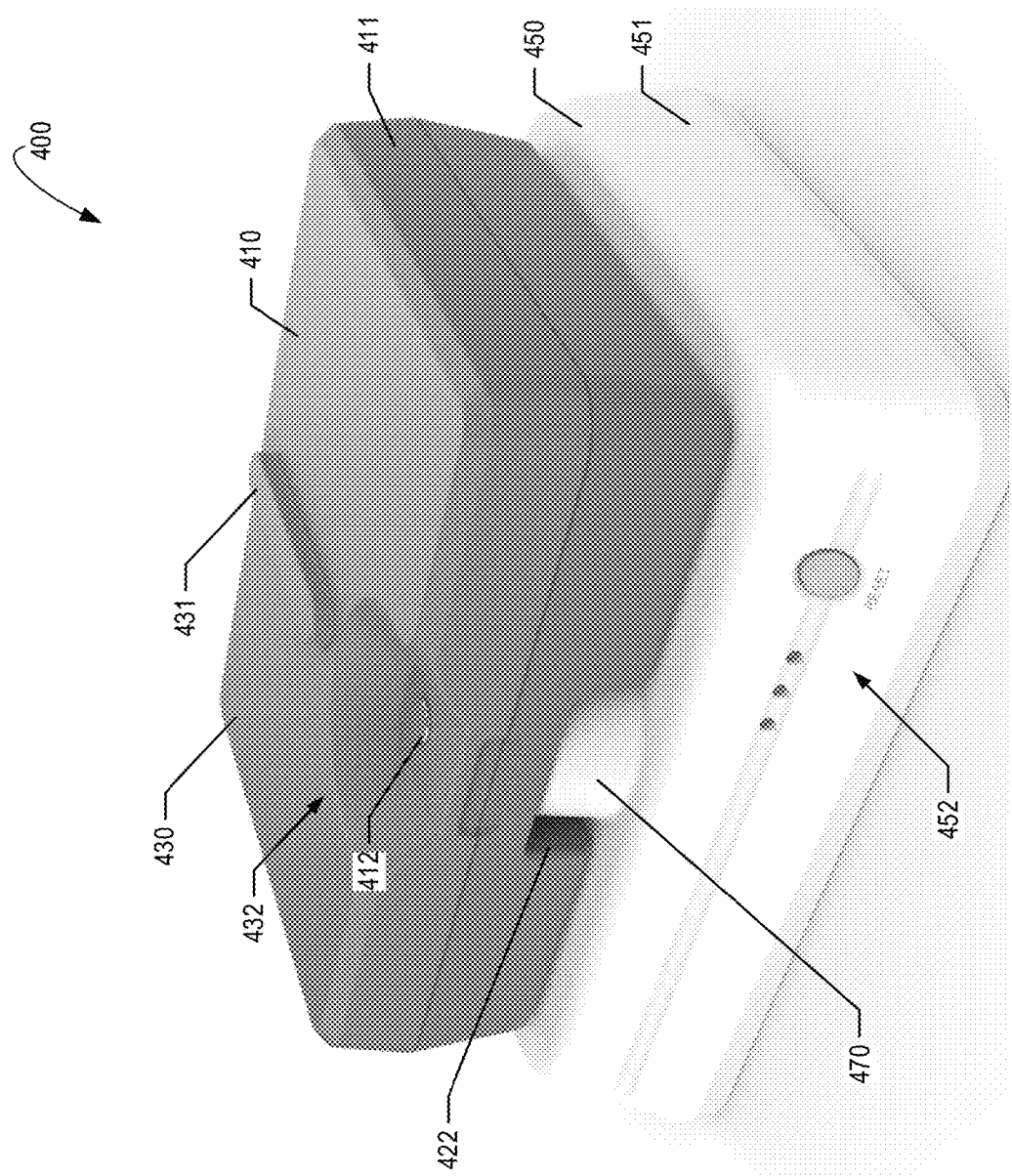
FIG. 4 is a perspective view of a container and cradle according to one embodiment.
Figure 5:
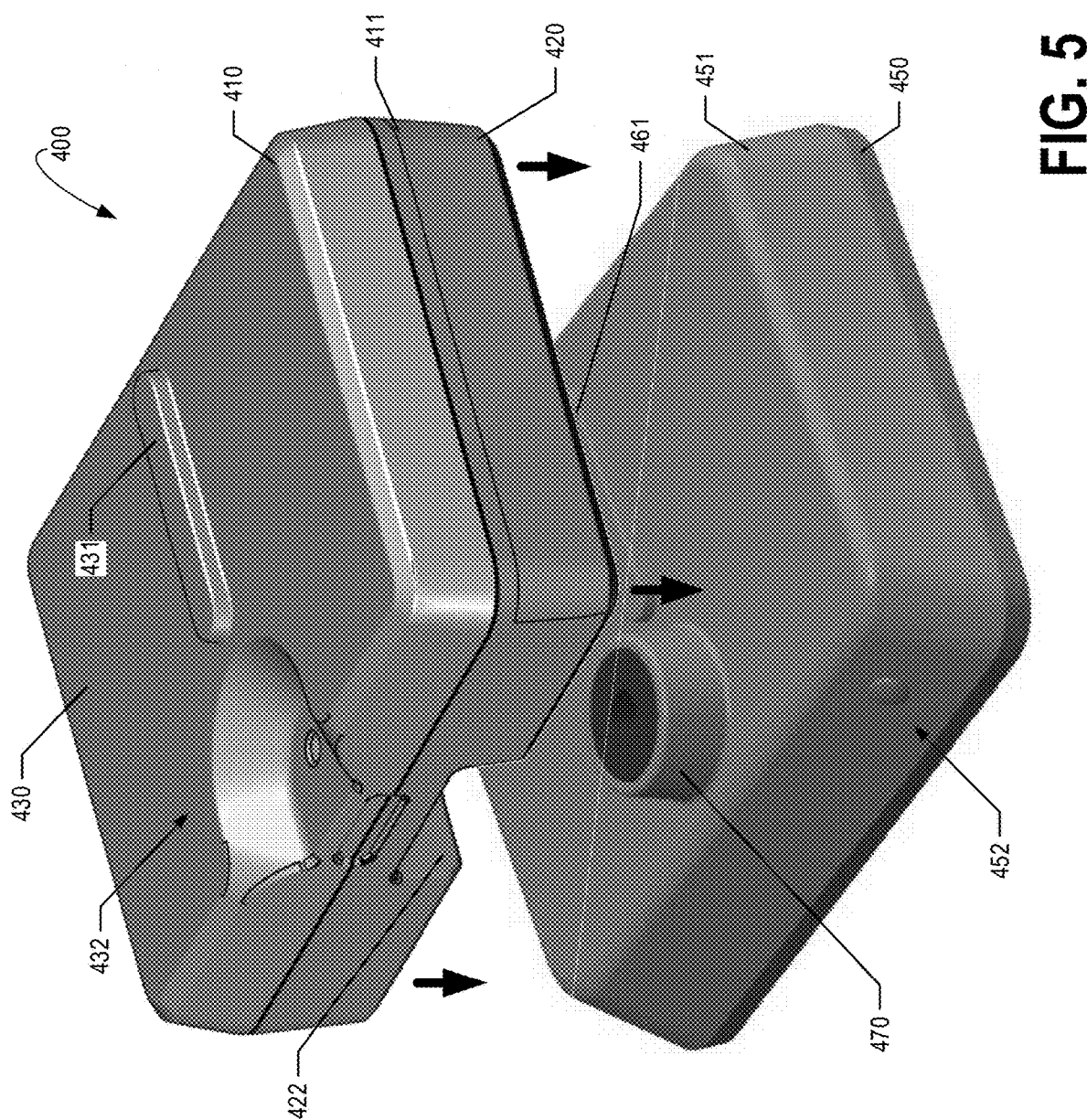
FIG. 5 illustrates a container being placed onto a cradle according to one embodiment.
Figure 6:
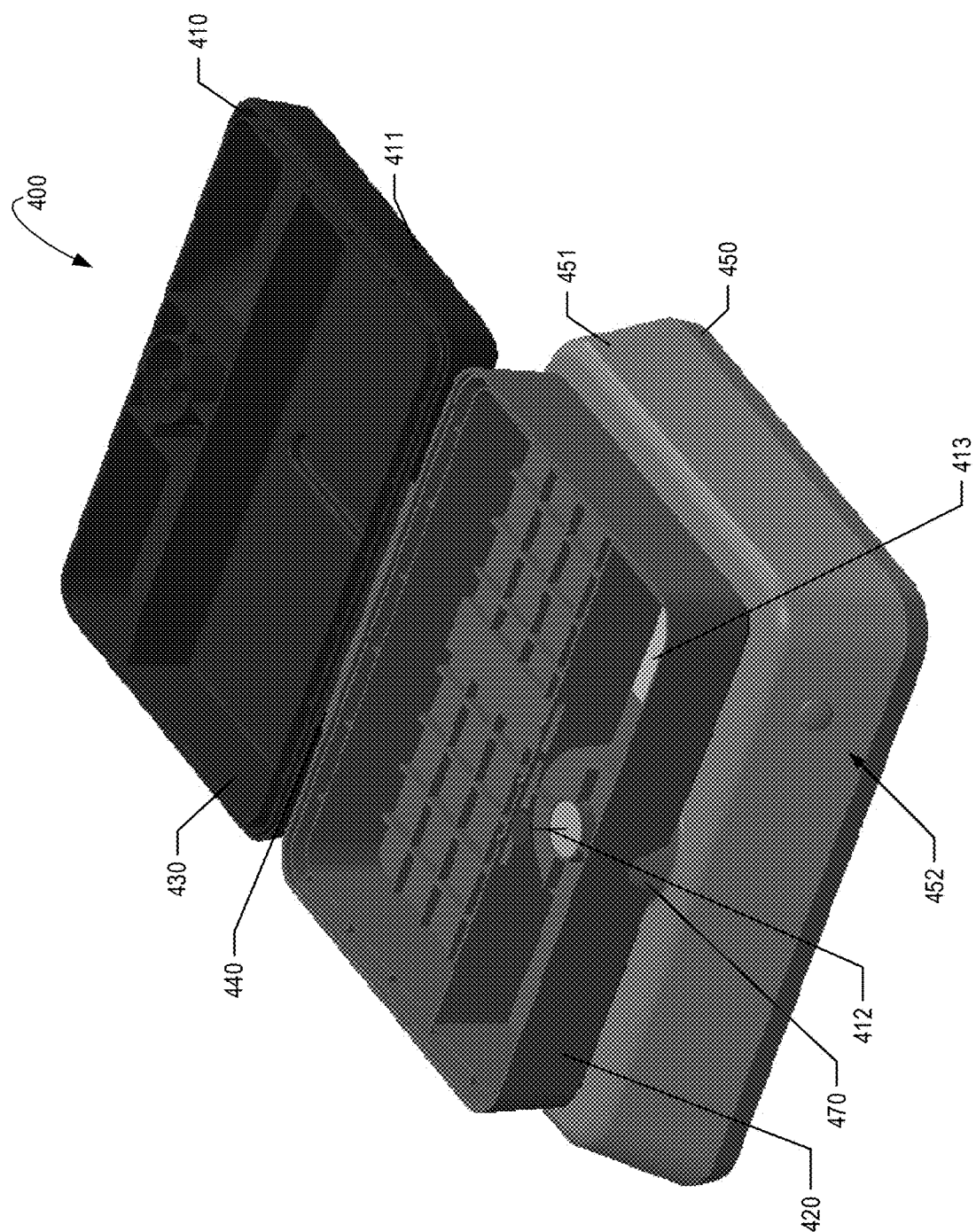
FIG. 6 illustrates a container in an open configuration on a cradle according to one embodiment.
Figure 7:
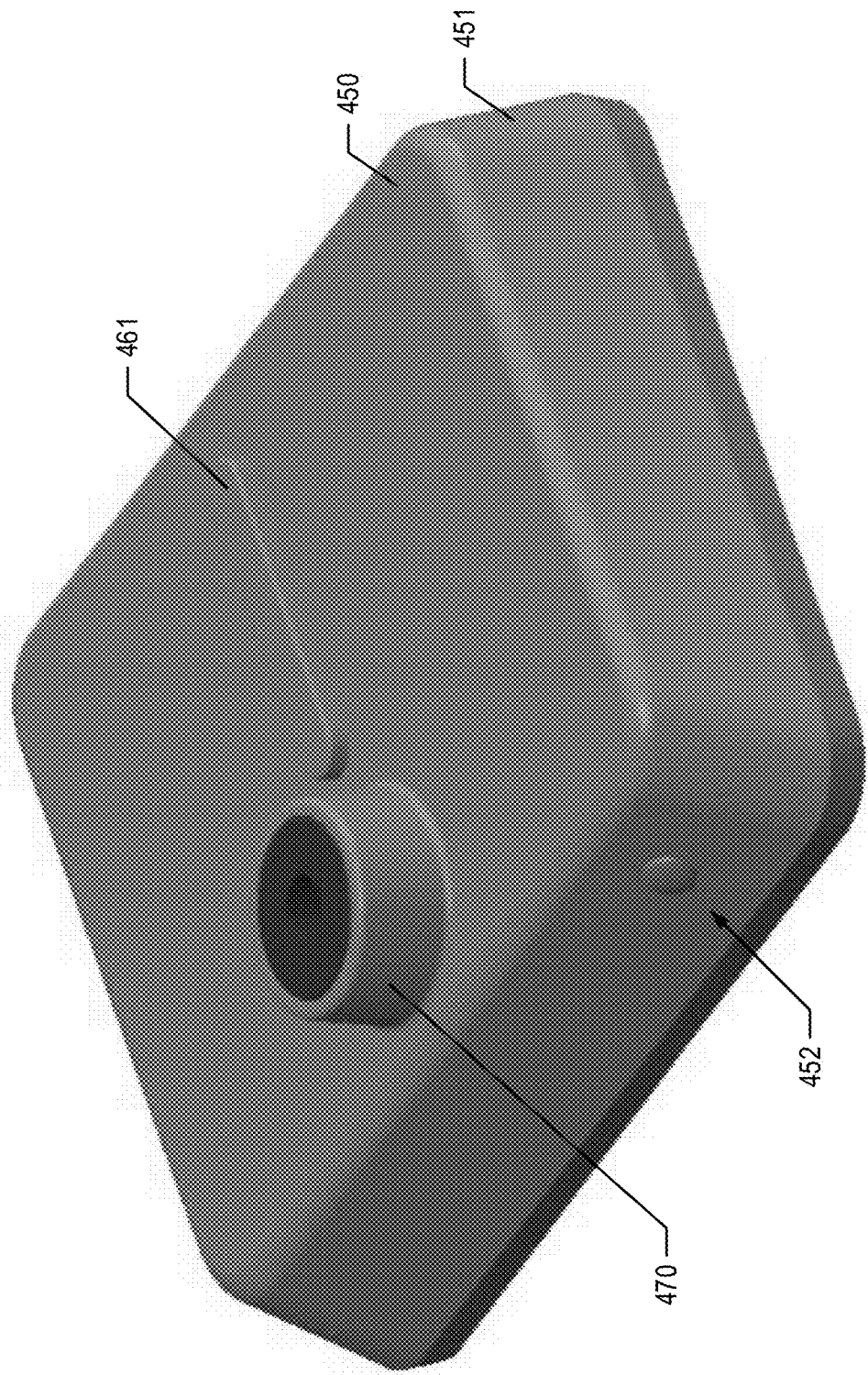
FIG. 7 illustrates a cradle according to one embodiment.
Figure 8:
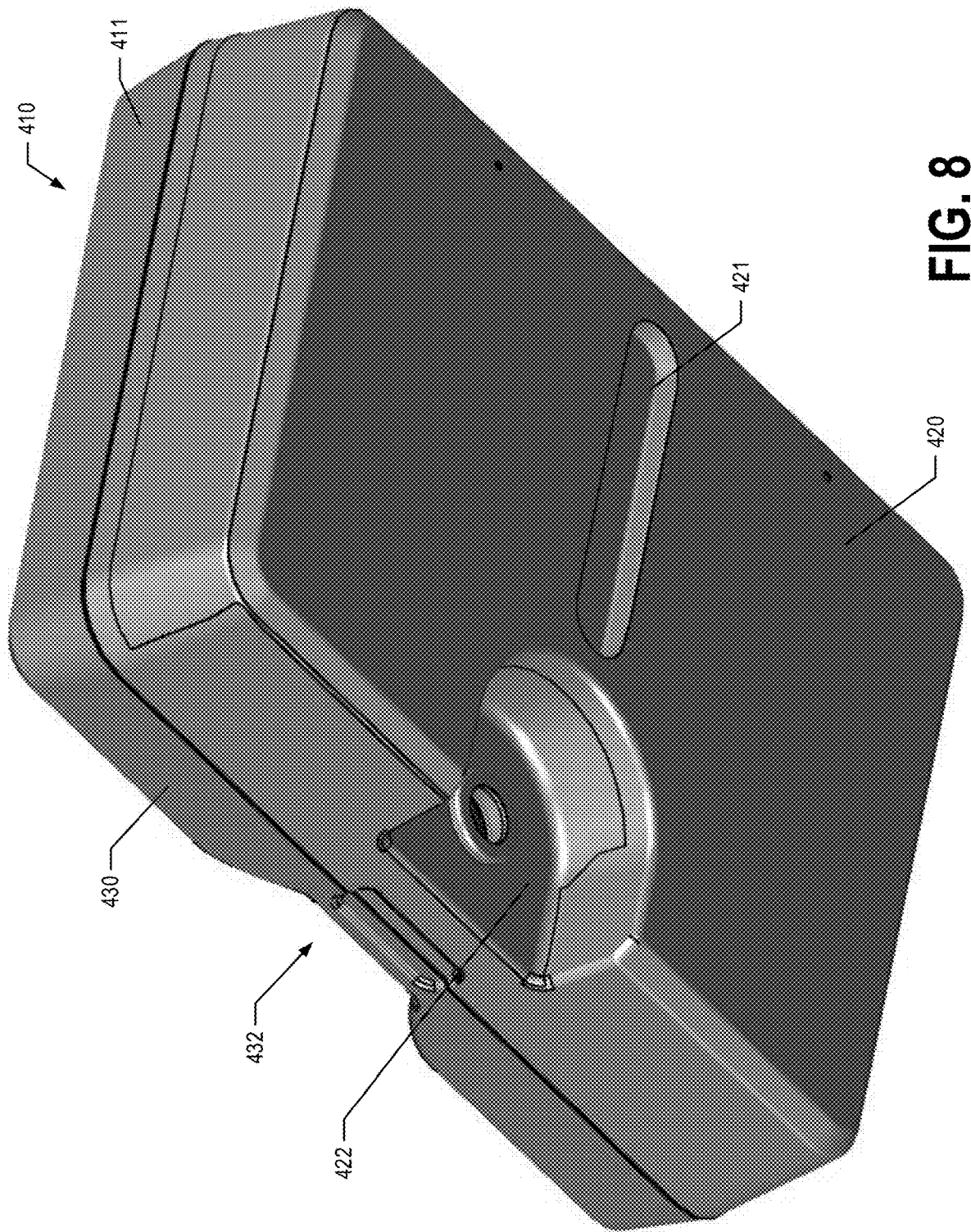
FIG. 8 illustrates a bottom perspective view of a container according to one embodiment.

The example container 410 is illustrated in additional detail specifically in FIGS. 6 and 8, with FIGS. 4, 5, and 7 illustrating the container 410 interaction with the cradle 450. Although illustrated as a single component of a multi-component secure supply system 400, it should be understood that in certain embodiments, the container 410 may embody an entire secure supply system 400, and may incorporate a self-actuating lock and various communication components for executing data communication processes as discussed herein in reference to the operation of the cradle 450.

As noted, the container 410 is configured for securely storing one or more objects therein. The container 410 includes a housing 411 that is configurable between a closed configuration (as shown in FIGS. 4-5, for example) and an open configuration (as shown in FIG. 6, for example). The container 410 additionally comprises a lock 412 configured to secure the container 410 in a locked configuration. As shown in FIG. 6, the container 410 additionally comprises a container identification module 413 comprising readable data indicative of a container identifier. As discussed in later detail herein, the container identification module 413 may comprise an RFID transmitter (e.g., an active RFID transmitter with onboard power supply or a passive RFID transmitter configured for receipt of external power to enable transmission, such as receipt of power from the cradle 450 via inductive power transmission, contact-based power transmission, and/or the like).

The container housing 411 may comprise a rigid material, such as a plastic material, a metal material, a composite material, and/or the like. The container housing 411 may be an opaque material such that users may be unable to see into the interior of the container. In other embodiments, the entirety of the container housing 411, or a portion of the container housing 411 may be transparent or translucent so as to enable viewing of the interior contents of the container 410. In various embodiments, all or a portion of the container housing 411 may be colored (e.g., red, blue, green, yellow, black, brown, and/or the like), and the color may be utilized as a container identification module 413 (detected via an optical color sensor). The container housing 411 may be sufficiently strong to impede unauthorized access to the container interior. However for those embodiments in which a container identification module 413 is placed within the interior of the container housing 411, the container housing 411 (or a portion thereof) may be transmissive, to enable a reading mechanisms of the cradle 450 to detect the identifying data of the container identification module 413. For example, the container housing 411 (or a portion thereof) may be radio-transmissive, so as to enable transmission of RFID signals. In other embodiments, the container housing 411 (or a portion thereof) may be transparent or translucent to enable optical transmission through the container housing 411.

As shown in the figures, the container housing 411 is configurable between a closed configuration and an open configuration. In the illustrated embodiment, the container housing defines a lower portion 420 and an upper portion 430. The lower portion 420 and upper portion 430 may be pivotably connected at a hinge portion 440. In certain embodiments, the container housing 411, including the lower portion 420, the upper portion 430, and the hinge portion 440 may be embodied as a single, unitary piece (e.g., manufactured via a single injection molding process, a single 3D printing process, and/or the like). In other embodiments, the lower portion 420, the upper portion 430, and the hinge portion 440 may be secured relative to one another, for example, via fasteners (e.g., adhesive, screws, bolts, rivets, welds, and/or the like).

It should be understood that the container 410 may be operable between a closed configuration in which access to the interior of the container 410 is prevented, and an open configuration in which access to the interior of the container 411 is enabled, via any of a variety of configurations of the container housing 411, while allowing selective locking in the closed configuration. As other examples, an upper portion 430 may be slidable relative to a bottom portion 420, an upper portion 430 may be entirely separable from the bottom portion 420, and/or the like.

As noted, the container housing 411 is selectably lockable in a closed configuration. Accordingly, the container 410 comprises a lock 412. The lock 412 may comprise a mechanical lock that may be actuated via an external device (e.g., an electromechanical unlocking mechanism of a cradle 450, as discussed in greater detail herein). In certain embodiments, the lock 412 may be unlocked via a specially configured unlocking mechanism, such as a key. The key may comprise a physical key that may be inserted into a portion of the lock 412, one or more magnetic (e.g., electromagnetic) components having a unique orientation to magnetically activate portions of the lock 412 (e.g., by generation of an electromagnetic field) that, when activated, configure the lock from a locked configuration to an unlocked configuration. As yet other examples, a key may comprise a series of indentions, protrusions, and/or other engagement features oriented and configured to engage corresponding features of the lock 412 such that, when each of the engagement features engage with corresponding features of the lock 412, the lock is configured from the locked configuration to an unlocked configuration. Moreover, as discussed herein, the engagement features, when engaged with corresponding features of the lock 412 so as to configure the lock to an unlocked configuration, may simultaneously prevent removal of the container 410 from the cradle 450, thereby locking the container 410 onto the cradle 450 while the container 410 is in the unlocked configuration. Such features may enable additional control over access to the interior of the container 410 by limiting access to a time period during which the container 410 is connected with the cradle 450. Moreover, such configurations enable the cradle 450 to monitor access times, such as a time at which the container 410 is configured to an unlocked configuration, and a time at which the container 410 is configured to a locked configuration, thereby enabling the cradle 450 to track an elapsed time during which the container 410 is unlocked. Such data may be stored locally or may be transmitted to the management computing entity 20 for storage in association with a user profile associated with the user accessing the interior of the container 410.

In certain embodiments, the lock 412 may be biased to a locked configuration, such that the lock 412 locks the container 410 in the closed configuration when the key is disengaged and the container 410 is closed. For example, the container 410 may be opened while under specified conditions (e.g., meeting certain specified criteria as discussed herein) and while connected with the cradle 450. If the container 410 is removed from the cradle 450 while open and then subsequently closed, the container 410 locks upon closure. However, as discussed herein, in certain embodiments the container 410 may not be removed from the cradle 450 while open and unlocked to avoid unauthorized access to the contents of the container 410 after initial unlocking.

As illustrated in the figures, the container housing 411 defines a top surface (defined as a part of the upper portion 430) and an opposite lower surface (defined as a part of the lower portion 420). The container housing 411 additionally defines sidewalls extending between the upper surface and the lower surface to define an entirely enclosed container 410. The sidewalls may be partially defined by each of the bottom portion 420 and the upper portion 430. Although not shown, it should be understood that certain embodiments may define one or more vents to allow controlled air exchange between a defined interior of the container 410 and a surrounding environment.

As shown specifically in FIG. 8, the lower surface of the illustrated container housing 411 defines an engagement feature 421 (e.g., an indention) matching a corresponding alignment feature of the cradle 450. Although illustrated as an indention, it should be understood that the engagement feature 421 may have any of a variety of embodiments, such as a protrusion, a series of indentions in a specific orientation, a series of protrusion in a specific orientation, and/or a combination thereof. The alignment feature 461 may be configured to facilitate placement of the container 410 onto the cradle 450 in an appropriate position to enable the cradle 450 to unlock the lock 412 of the container. Moreover, the upper surface may have a corresponding alignment feature 431 matching the alignment feature of the cradle 450, so as to engage the engagement feature 421 of the lower surface. The alignment feature 431 of the upper surface is thus configured to enable secure stacking of a plurality of containers 410.

Moreover, as discussed in greater detail herein, the engagement feature 421 of the bottom surface, and the corresponding alignment feature of the cradle may be configured to have a selectably locking engagement, such that the container 410 may be locked onto an upper surface of the cradle 450 while the container 410 is in an unlocked configuration. Thus, the cradle 450 may be configured to control access to various containers 410, such that a container 410 may only be unlocked while secured onto the cradle 450, thereby impeding simultaneous access to a plurality of containers 410 accessed via a single cradle 450. However it should be understood that in other embodiments, the cradle 450 may be configured to selectably and lockably engage the lock 412 of the container to provide analogous features, such that the lock 412 is locked to the cradle 450 while the container 410 is in an unlocked configuration. Locking the lock 412 simultaneously unlocks the container 410 from the cradle 450 in such embodiments.

As shown, the container housing 411 additionally defines a cavity 422 within the lower portion 420 configured to at least partially surround an unlocking portion of cradle 450. The cavity 422 further facilitates alignment of the container 410 relative to the cradle 450, moreover, the cavity 422 (together with a corresponding cavity 432 within an upper portion 430), provides a thinned overall height of the container housing 411, thereby shortening the distance between opposing upper and lower surfaces of the container housing 411 and thereby shortening an effective distance for a lock to extend through the entire height of the container housing 411.

Overall, the container housing 411 defines a hollow interior portion. The lower portion 420 and the upper portion 430 may each be hollow and have an open side, such that placement of the lower portion 420 and the upper portion 430 in the closed configuration collectively defines a continuous hollow interior volume within the container housing 411. As shown specifically in FIG. 6, the interior of the container housing 411 (e.g., specifically, portions of the lower portion 420) may define one or more individual apertures, enclosures, cubbies, trays, segments, or other segmented portions thereof. Each of the individual, segmented storage areas within the interior of the container housing 411 may be individually sealed (e.g., with a plastic sealed puncture-opening film, a foil-based puncture-opening film, a peel-to-open film, and/or the like) so as to ensure that small, individual objects (e.g., small pills) remain secure within the container housing 411, even when subject to movement and/or jostling. It should be understood that the interior volume of the container housing 411 may have any of a variety of configurations, provided to appropriately support or otherwise contain an object to be placed therein. For example, the interior volume may be subdivided into two or more portions, the interior volume may have one or more object-supporting inserts (e.g., a foam insert, a thermoformed insert, and/or the like) to securely hold an object in a specific position within the interior of the container housing 411, and/or the like.

As discussed above, the container 410 additionally comprises a container identification module 413 comprising data indicative of the container identity. In certain embodiments, the container identity may be embodied as the identity of the contents of the container 410. In other embodiments, each container identifier may be unique, and the container identifier may be mapped to the contents of the container 410 (e.g., within a data table stored within a memory storage area (e.g., associated with the cradle 450, associated with the management computing entity 20, and/or the like).

The container identification module 413 may be embodied as an RFID tag (active or passive), a QR code, a barcode, a container color, or any other readable characteristic of the container 410 that may be correlated with a container identifier. The container identification module 413 may be secured onto an exterior of the container 410, embedded within a surface of the container 410, placed within the interior of the container 410, and/or the like. The container identification module 413 may be permanently associated with a particular container 410, or may be replaceable such that the container identification module 413 for a particular container 410 may be removed and replaced so as to change the container identifier associated with the container 410. In other embodiments, the container identification module 413 may be provided as a portion of an object placed within the container 410 (or packaging of the object). As an example, a prescription medication bottle may contain an RFID tag providing an identification of the medication contained therein, and the prescription medication bottle may be placed within the container 410 such that the RFID tag associated with the medication bottle is readable through the container 410 so as to be associated therewith.

In certain embodiments, at least a portion of the container housing 411 may be shielded to electromagnetic signals, radio signals, and/or the like, so as to avoid potentially crossing signals between multiple containers. In such embodiments, the container housing 411 may define a shielding window area in which the housing does not include such shielding, such that signals may pass through the shielding window area for transmission to the cradle 450. Such embodiments further impede unauthorized access to the interior of the container 410 though attempted signal crossing between a container 410 for which access is authorized with a container 410 for which access is not authorized.

In certain embodiments, one or more containers 410 may define signal pathways, such as conductive portions therein, for enabling signals to pass from a first container 410, through a second container 410, to a cradle 450. In such embodiments, the signal pathways of each of the plurality of containers 410 within a stack of containers 410 may operate as a signal bus along which signals may be transmitted from the cradle 450 to specific containers 410.

Such embodiments may enable a plurality of containers 410 to be stacked on top of one another and onto the cradle 450, while enabling the cradle to simultaneously control access to an interior of each of the plurality of containers 410. In such embodiments, each of the containers 410 may incorporate a self-actuating lock 412, such that the self-actuating lock is configured to unlock upon receipt of appropriate signals transmitted from the cradle 450. In such embodiments, the cradle 450 may generate appropriate signals for unlocking only a single, identified container within a stack of a plurality of containers 410, thereby enabling access only to the container 410 for which the user is authorized to access. Such configurations may additionally enable a cradle 450 to simultaneously unlock a plurality of containers 410 within the stack of containers 410, thereby enabling the user to access the interior of a plurality of containers 410 simultaneously.

Moreover, although the container 410 discussed herein is described as having a single lockable interior portion, it should be understood that in certain embodiments, a container 410 may comprise a plurality of independently lockable (and unlockable) compartments that may be accessed based at least in part on independently applicable access criteria. It should additionally be understood that access to multiple compartments of a single container may be provided in a defined order, such that a user must access a defined first compartment before accessing a defined second compartment. Such embodiments may be implemented such that an access criteria of the second compartment comprises an indication (e.g., to be stored within the cradle, within a user profile, and/or the like) that the user previously accessed an interior of the first compartment, such as based on data generated and/or stored indicating that the first compartment of the container was previously accessed in association with a defined user identifier. As discussed in greater detail herein, analogous sequential access criteria may be utilized for multiple, separate containers (e.g., wherein access to a particular container, rather than a compartment of a container, is dependent on previous access to a particular container).

b. Exemplary Cradle

As noted above, the containers 410 are configured to engage and interact with a cradle 450 to enable selective unlocking of the container 410 to enable access to objects stored therein. As shown, the cradle 450 comprises a cradle body 451 defining an upper surface for supporting one or more containers 410 thereon, an opposite lower surface for resting on a support surface, and sidewalls extending between the upper surface and the lower surface. At least one of the sidewalls (e.g., a front sidewall) may comprise one or more user interface elements 452, such as buttons, identifiers (e.g., lights) providing information regarding an operational status of the cradle 450. As just one example, an identifier may indicate whether the cradle 450 is successfully communicating with a network, whether the cradle 450 recognizes a container 410 placed thereon, whether the cradle 450 has unlocked the container 410, and/or the like. The user interface elements may additionally comprise a reset button, which may restart one or more processors, network communication modules, and/or the like of the cradle 450. In certain embodiments, the cradle 450 may receive power from an external power source, and thus the cradle body 451 may have a power cord (not shown) extending therefrom.

As discussed above, the upper surface of the cradle 450 may define one or more engagement features 461 configured to engage with corresponding engagement features 421 of the container 410. The engagement features 461 may facilitate placement of the container 410 onto the upper surface of the cradle 450 to enable the cradle 450 to operate the lock 412 of the container 410 when access to the interior of the container 410 is granted.

Moreover, the cradle 450 comprises at least one computing system comprising one or more processing entities, one or more communication modules, one or more memory storage areas, and/or the like. As discussed in greater detail herein, the one or more processing entities are configured for identifying signals received via the one or more communication modules, such as signals provided from a container 410, signals provided from one or more biosensors (e.g., stand-alone biosensors, biosensors integrated with the cradle body 451, biosensors integrated with user computing entities 10, and/or the like), signals provided from the management computing entity 20, and/or the like. Moreover, the one or more processing entities of the cradle 450 may be configured for generating signals to be provided to one or more containers 410, and/or for generating signals to operate an unlocking mechanism 470 of the cradle 450 to unlock a connected container 410.

In certain embodiments, the communication modules may comprise one or more network communication modules, such as wired network communication modules, wireless network communication modules (e.g., Wi-Fi, 3G, LTE, 5G, and/or the like), and/or the like. Example network communication modules are discussed herein in reference to the management computing entity 20. The communication modules may additionally comprise Bluetooth, NFC, infrared, and/or other close-range wireless communication modules for communicating with various biosensors (or user computing entities 10 having integrated biosensors), so as to receive biosensor signals therefrom. The communication modules may additionally comprise one or more container identifier reader modules, such as RFID readers (for reading active and/or passive RFID tags), optical readers, such as color sensors for detecting a color of a container, infrared sensors for reading barcodes, cameras for reading QR-codes, pre-human-readable tags (the cameras operating together with optical-character recognition (OCR) systems), and/or the like. It should be understood that any of a variety of container identifier reader modules may be provided as necessary for reading specifically configured container identifier modules 413.

As additionally discussed herein, the cradle 450 comprises an unlocking mechanism 470. The unlocking mechanism 470 may be embodied as a mechanical, electromechanical, magnetic, electromagnetic, or other mechanism for engaging and interacting with locks 412 on containers 410. In other embodiments, the unlocking mechanism 470 may comprise a signal transmitter for transmitting unlock signals to containers 410 having integrated self-actuating locking mechanisms (such as in embodiments enabling control over a plurality of containers 410 simultaneously by a single cradle 450.

As just one example, an unlocking mechanism 470 may comprise an electromechanical device having an integrated key that may be utilized to interact with a corresponding feature of a container's lock 412 to selectively unlock the container 410. As yet another example, the unlocking mechanism 470 may comprise an electromagnetic device configured to apply magnetic forces to a container's lock 412 to engage the lock 412 and unlock the container 410.

In those embodiments in which the unlocking mechanism 470 is configured to generate and transmit unlocking signals to self-actuating locks 412 of specific containers, the unlocking signals may comprise a code (e.g., a character string) utilized as an unlocking code for a container 410, and a container identifier, such that the appropriate container 410 executes the unlock command corresponding to the received code. In other embodiments, each container 410 may be assigned a unique unlocking code, such that a container 410 will only unlock upon receipt of the unique unlocking code. Other containers 410 receiving the same unlocking code (e.g., via wired or wireless communication from the cradle 450) will not unlock. Such configurations enable a plurality of containers 410 with corresponding locks 412 to be connected on a common communication bus (e.g., established by conductors between the containers 410 as discussed above), such that the cradle 450 may transit a single unlock signal along the common bus to cause only a select container 410 to be unlocked.

Moreover, the cradle 450, through the engagement feature 461 and/or the unlocking mechanism 470 may be configured to selectively lock a container 410 onto the cradle 450 while the container 410 remains unlocked. This container connection lock functionality enables the cradle 450 to maintain additional control over access to the interior of the container 410 by monitoring when the container is unlocked and accessible to the user. The processing entities may utilize such features to record unlock times and lock times for a particular container 410, and such data may be provided to the management computing entity 20 for storage (e.g., in association with a user Electronic Medical Record (EMR)) and/or for providing notifications to appropriate personnel (e.g., a physician or other medical personnel).

IV. Exemplary System Operation

Figure 9:
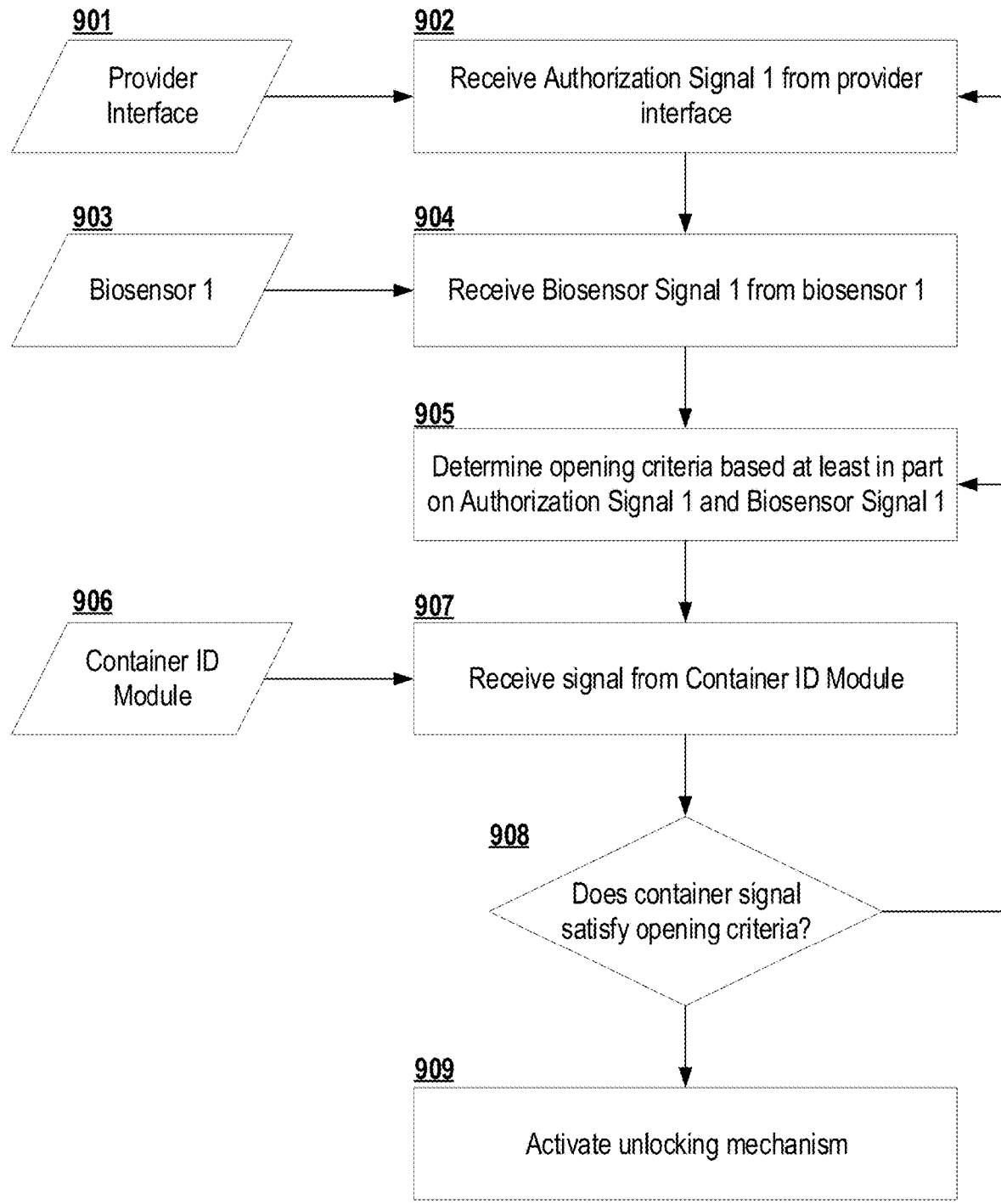
FIG. 9 is a flowchart indicating an example operation of certain embodiments.
Figure 10A:
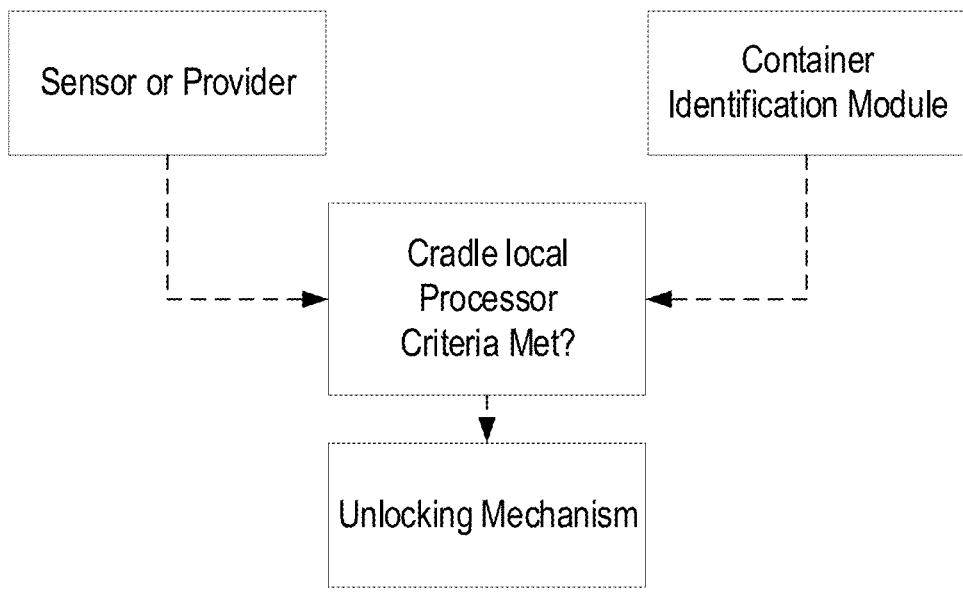
FIGS. 10A-10C illustrate alternative example communication configurations between computing entities according to certain embodiments.
Figure 10B:
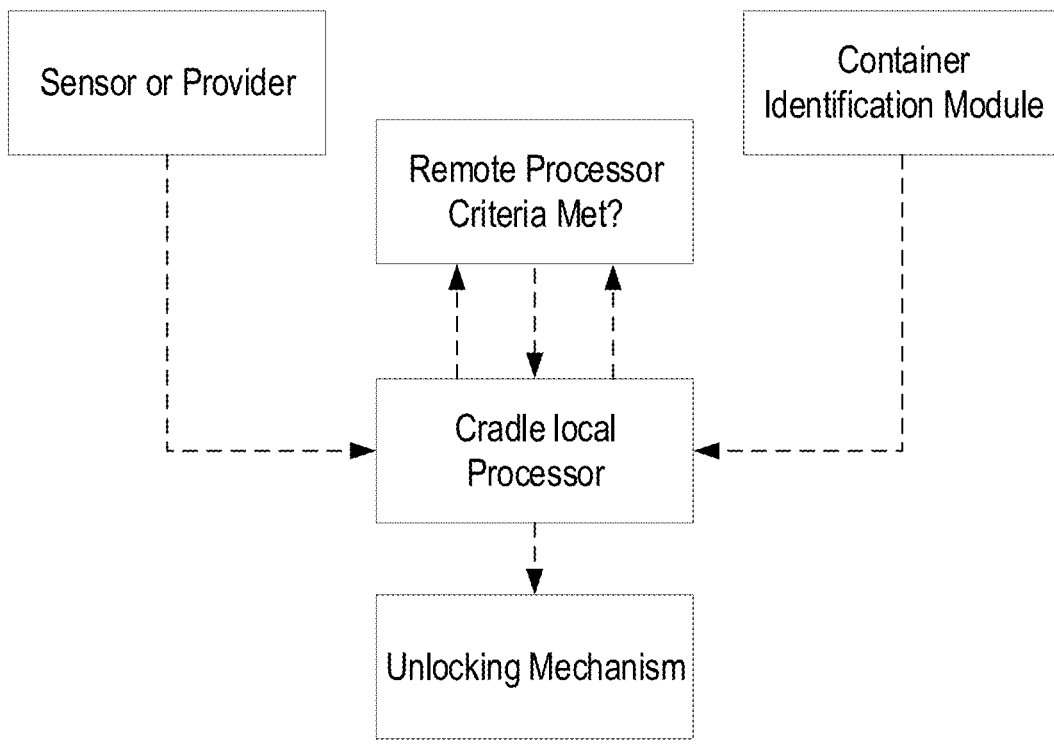
Figure 10C:
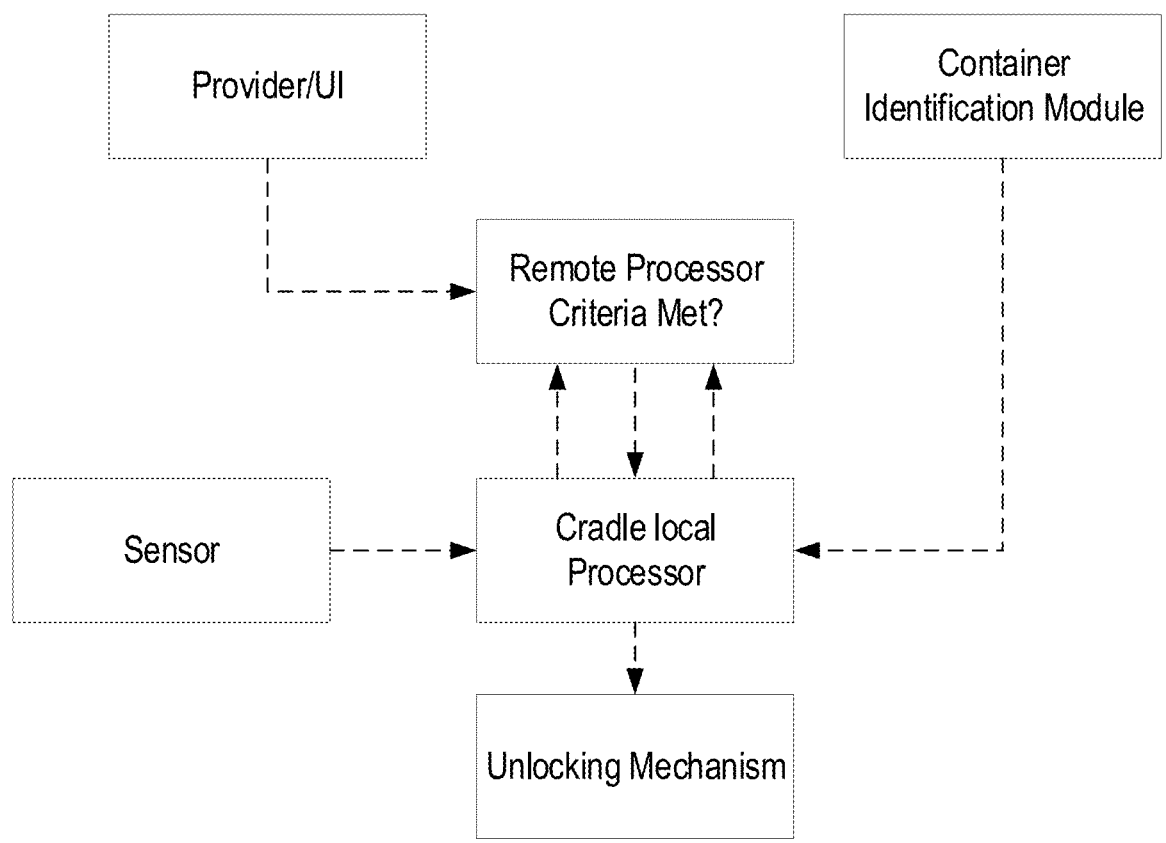

Details regarding the operation of various embodiments is discussed in reference to the flowcharts of FIGS. 9-10C, with additional reference to the illustrated configurations of FIGS. 4-8. As discussed herein, various embodiments provide physicians and/or other care providers with a greater degree of control in providing various objects (e.g., prescription medication, diagnostic tools, and/or the like) to end users while controlling access to those objects in accordance with specified access criteria. Specifically, a particular object may be provided to a user within a locked container, and the locked container may be unlocked in accordance with the indicated specified access criteria (also referred to herein as unlock criteria), which may be based at least in part on criteria established by the physician or other care provider, data stored within an EMR (or other collection of stored data attributable to the user), biosensor signals generated by one or more biosensors measuring characteristics of the user's body, historical biosensor signals indicative of historical characteristics of the user's body as measured by the biosensors, and/or the like.

Moreover, various embodiments enable the implementation of conditional prescriptions (e.g., for medication)—a prescription that becomes effective contingent on one or more circumstances being met. For example, a prescriber physician/care provider may issue a prescription for an antipyretic drug contingent on a patient user having a fever. In the remote practice of medicine, it would be useful for the antipyretic to be automatically dispensed when a signal from a thermometer indicated the patient had a fever rather than requiring the physician/care provider to personally verify the patient user's temperature. In certain embodiments, by utilizing biosensors associated with the patient, the determination of whether the patient has a fever may be based at least in part on historical biosensor data (e.g., historical temperature data), thereby establishing a patient-specific threshold for establishing whether the patient has a fever. For example, if a particular patient's body temperature is historically high, a fever determination may be triggered at a higher sensed temperature than a second patient whose body temperature is historically low.

In certain embodiments, the physician/care provider may cause generation of an authorization signal by providing appropriate user input to a user interface accessible via a user computing entity 10. The authorization signal may define a container 410 (or container type) to be unlocked (e.g., by specifically defining contents of a container to be unlocked). The authorization signal may also define one or more criteria for accessing the interior of the container, such as specific biosensor signals, data indicating a particular historical biosensor data trend over a particular historical time period (e.g., indicating a patient's temperature is trending upward, indicating a patient's blood-oxygen level is trending downward), data indicating a specific prior history of access to other objects within containers, and/or the like. Such criteria may be satisfied before or after generation of the authorization signals. Moreover, the authorization signal may identify a particular user (e.g., by a user identifier) for which the authorization signal applies.

The management computing entity 20 receiving the authorization signal may identify a cradle 450 (having a corresponding cradle identifier) associated with the user for which the authorization signal is generated, and may transmit a remote signal to the cradle 450 to enable unlocking of a particular container 410 (or type of container 410, defined based at least in part on the contents of the container 410).

Examples of biosensor signals are numerous. Possible biosensor signals may be embodied as heart rate or pulse signals generated by corresponding biosensors, breathing rate signals generated by corresponding biosensors, blood pressure signals generated by corresponding biosensors, glucose concentration signals generated by corresponding biosensors and/or the like. Other example biosensor signals may comprise electronically received blood test results, disease test results, DNA sequencing results, and/or the like. As just one specific example, biosensors may comprise a thermometer and/or a pulse oximeter.

As other examples, data indicative of biosensor signals may be compiled (e.g., in a memory storage area associated with a cradle, in a memory storage area associated with a management computing entity 20, and/or the like) so as to establish a historical trend of data associated with the one or more biosensors. A historical trend may indicate a sequence of biosensor signal data generated by one or more biosensors. For example, a biosensor trend may indicate a patient's body temperature over time (which may be utilized to indicate whether the patient's body temperature is rising, falling, or maintaining a constant temperature). As another example, a biosensor trend may indicate a patient's blood-oxygen level over time (which may be utilized to indicate whether the patient's blood-oxygen level is rising, falling, or maintaining a constant level over time). Historical data of one or more biosensors may be established for any of a variety of other biosensor types as well, such as blood pressure monitors, glucose monitors, and/or the like.

It should be understood that access criteria may be based on a single biosensor signal satisfying a particular criterion, or multiple biosensor signals satisfying corresponding criteria. Such corresponding criteria may be based on a single measurement associated with a biosensor (e.g., a single temperature measurement being above a defined criteria threshold) and/or a trend (e.g., a historical trend showing a rate of temperature change being above a defined criteria threshold) for one or more biosensor signals. Biosensor signals may need to satisfy one or more criteria before triggering unlocking. For example, a temperature signal may be required to exceed a threshold value (indicative of a fever) and blood oxygen level signals (of a blood oxygen sensor) may need to fall below a threshold to unlock a COVID-19 test kit. Note that some embodiments may determine which containers are eligible to open based on the biosensor signal rather than simply confirming a selection made by a provider (as reflected within an authorization signal). As discussed, the biosensors (e.g., thermometer and/or pulse oximeter) may communicate with the cradle via a direct wireless communication protocol, such as a wireless Bluetooth connection (or other wireless communication protocols, such as NFC, infrared, and/or the like). The cradle 450 may then be configured to perform local determinations of whether a particular container 410 is to be unlocked based on received biosensor signals, received authorization signals, received container identification data, and/or other data received from one or more remote storage areas. In other embodiments, the cradle 450 may transmit the biosensor signals and/or the container identification data to the management computing entity 20 (e.g., via a wireless communication protocol, such as a cellular-based wireless communication protocol) to enable the management computing entity 20 to determine whether the container should be unlocked.

As discussed herein, any of a variety of technologies may be utilized to determine container identity. As non-limiting examples, RFID and visual pattern readers may be utilized to obtain container identification data from container identification modules in certain embodiments. As another example, NFC technologies operable at close ranges may be utilized for transmitting container identification data from a container identification module to a corresponding reader of a cradle 450. Moreover, non-limiting examples of visual pattern readers include bar code and QR code readers. Other forms of visual detection, such as color identification and text recognition may be employed as discussed herein.

It should be understood that the processing methodologies discussed herein (including determinations of whether a particular container should be unlocked) may be performed via any of a variety of processing resources, such as processing resources local to the cradle 450, cloud-based processing resources (e.g., at the management computing entity 20), and/or a combination thereof. FIGS. 10A-10C illustrate example processing configurations according to certain embodiments. It should be understood that the embodiments illustrated are merely examples, and other processing configurations may be utilized in certain embodiments. FIG. 10A illustrates a first example processing configuration in which biosensor signals, provider-specified authorization signals, and container identifier data are received by a local processor of the cradle 450, which determines whether to activate the unlocking mechanism based at least in part on unlocking criteria specified within the authorization signals. FIG. 10B illustrates a second example processing configuration in which biosensor signals, provider-specified authorization signals, and container identifier data are received by a local processor of the cradle 450. The local processor of the cradle 450 may then transmit the received data to a remote processing resource (e.g., of the management computing entity 20) for determination of whether to activate the unlocking mechanism based at least in part on the unlocking criteria specified within the authorization signals. The remote processing resource may then transmit a signal (e.g., an unlock signal) to the cradle 450 to cause the cradle 450 to activate the unlocking mechanism and unlock a container 410.

In the embodiment of FIG. 10C, biosensor signals and container identification signals are received by the local processor of the cradle 450, which relays those signals to a remote processing resource (e.g., of the management computing entity 20). The management computing entity 20 receives authorization signals provided from a user computing entity 10 associated with a provider. The remote processing resource may then determine whether to activate the unlocking mechanism based at least in part on the unlocking criteria specified within the authorization signals. The remote processing resource may then transmit a signal (e.g., an unlock signal) to the cradle 450 to cause the cradle 450 to activate the unlocking mechanism and unlock a container.

Moreover, although discussed herein as incorporating a cradle 450 encompassing processing resources and network communication modules, it should be understood that in certain embodiments, a container may comprise processing resources, such that the container may self-unlock without interaction with a separate cradle 450.

Moreover, it should be understood that the discussed methodologies may be performed as a part of a healthcare service system. In certain embodiments, data, such as biosensor data, may be collected as discussed herein, and may be provided to one or more care providers, for example, for enabling the care providers to provide customized care to the patient user. Moreover, in certain embodiments, data collected as discussed herein, including biosensor data, data indicating access to various objects, and/or the like, may be stored within EMR data (or other remotely stored data attributable to the patient user) so as to provide a more detailed view of the patient user's healthcare.

a. Example Process for Unlocking a Container

FIG. 9 illustrates an example process for unlocking a container 410 according to certain embodiments. As discussed above, the various processing steps may be performed at least partially via one or more processors of a cradle 450, via one or more processors of a management computing entity 20, via one or more processors of a user computing entity 10, or combinations thereof.

Certain embodiments may utilize stored profiles or other unique identifiers to enable routing of appropriate data between computing entities and/or to ensure that appropriate containers 410 are unlocked when appropriate. For example, users (e.g., patients) may each have a corresponding user identifier, which may be stored in association with additional data attributable to the user. For example, a user profile associated with the user identifier may comprise EMR data (or may comprise links to EMR data) associated with the user. The user profile may additionally comprise one or more cradle identifier indicative of a cradle 450 associated with the user. Such identifiers may be utilized such that appropriate authorization signals are routed to appropriate cradles 450 based on a physician's identification of a particular user for which an authorization signal applies. However, it should be understood that in certain embodiments, one or more cradles 450 may be publicly accessible (or otherwise accessible to a plurality of users), in which case a cradle 450 may be temporarily associated with a user (e.g., by the user providing identifying data to the cradle 450 upon requesting use thereof). As non-limiting examples, the cradle 450 may be temporarily associated with a user by the user providing user input indicative of the user's identity to a user interface of the cradle 450, by a user computing entity 10 associated with the user providing data indicative of the user's identity to the cradle 450 (e.g., via wireless communication), by a biosensor associated with the user providing data indicative of the identity of the user to the cradle (e.g., via wireless communication, and/or the like).

Moreover, in certain embodiments unique container identifiers (or container type identifiers) may be associated with identified contents thereof. Such configurations enable an authorization signal to identify either a container identifier of the contents of a container 410, and processing resources may thereby determine whether a specific container identifier (e.g., a container identifier associated with a container 410 secured relative to a cradle 450) satisfies applicable access criteria. As noted, particular containers 410 may be reusable, and accordingly the container identifiers may be reassigned to different container contents that may be reflected within a mapping data table or other association system for associating data indicative of the contents of a container with a container identifier. In other embodiments, a container identifier may be replaced with a reusable container, such that the container identifier is indicative of the contents of the container on/in which it is placed.

With reference now to FIG. 9, a method as discussed herein may begin as reflected at Block 901, via a provider interface provided to a user computing entity 10 associated with a care provider. The provider interface is configured to receive user input indicative of an authorization signal to be provided for a particular user, and accordingly the provider interface may receive data indicative of a user (e.g., a user identifier) for which the authorization signal is to be provided, an object (e.g., a medication, a diagnostic test, and/or the like) for which the authorization signal relates, and one or more criteria for limiting access to the object (e.g., biosensor-based criteria, historical object access based criteria, and/or the like). As an example, a biosensor-based criteria may be embodied as a minimum threshold body temperature of the user, a maximum threshold body temperature of the user, a minimum blood oxygen level measurement of the user, a maximum blood oxygen level measurement of the user, and/or the like. The biosensor-based criteria may comprise a plurality of biosensor-based criteria (e.g., a minimum body temperature combined with a maximum blood-oxygen level). In certain embodiments, the provider interface may only enable selection of biosensor-based criteria for which a user is known to have a biosensor capable of generating such measurements (e.g., based on data indicative of available biosensors for the user, as stored within a user profile). As yet other examples, a historical object access based criteria may be utilized to enable a care provider to provide a sequential prescription of objects to a user, such that a user is required to access a first object within a corresponding container 410 (or a first compartment of a container 410) before the user is able to access a second object within a second corresponding container 410 (or within a second compartment of the same container 410, such as where a single container comprises both the first compartment and the second compartment). In such embodiments, the user profile (or EMR data, as applicable) may store data indicative of historical object access, so as to enable determinations of whether the user is complying with applicable historical object access.

Upon completion of receipt of user input to the provider interface, the user computing entity 10 associated with the provider may transmit the data to an appropriate receiving computing entity. As discussed herein, the authorization signal generated based at least in part on the provider's user input may be transmitted to the cradle 450 for local processing therein, to management computing entity 20 for processing, and/or to other processing resources according to the specific configuration of the embodiment. As discussed herein, data indicative of the user for which the authorization signal applies may be utilized to identify an appropriate routing location for transmitting the authorization signal, such as by identifying an appropriate cradle 450 for receipt of the data. The transmission of the authorization signal may thus proceed to transmit the data to the appropriate identified recipient of the data.

Although not shown in FIG. 9, it should be understood that in certain embodiments, the authorization signal may additionally be configured to initiate additional processes as required by a healthcare system. For example, as the authorization signal identifies a particular object (e.g., a medication) applicable to the authorization signal, certain embodiments (e.g., the management computing entity 20) may review data within a user profile to determine what objects are available to the user (e.g., within corresponding containers 410). The data indicative of objects available to the user may be updated based at least in part on data received from a cradle 450 associated with the user indicating container identifiers that have been connected (and which remained locked) to the cradle 450. However, such data may be updated from any of a variety of data sources, such as shipping data indicative of containers 410 sent to the user, pharmacy data indicative of containers 410 obtained by the user, and/or the like. Based at least in part on the authorization signal and data indicative of objects available to the user, the authorization signal may be utilized to initiate an order to send an applicable object to the user upon determining that the applicable object as identified within the authorization signal is not available to the user.

With reference again to FIG. 9 and as indicated at Block 902, the authorization signal is received to enable a determination of whether a particular user is authorized to access a particular container 410. In certain embodiments, the authorization signal may indicate that access criteria specified therein must be satisfied after generation of the authorization signal (such authorization signals may enable conditional prescriptions or conditional access to objects). For example, if one or more biosensor-based criteria are specified, the biosensor-based criteria may only be satisfied with biosensor signals received/generated after generation of the authorization signal (e.g., as determined based at least in part on time stamps, and/or as determined based on receipt of biosensor signals after receipt of the authorization signal). In other embodiments, the authorization signal may indicate that access criteria specified therein may be satisfied before or after generation of the authorization signal (such authorization signals may enable a second variation on conditional prescriptions or conditional access to objects). For example, if one or more biosensor-based criteria are specified, the biosensor-based criteria may be satisfied with biosensor signals received and stored prior to generation/ receipt of the authorization signal. In yet other embodiments, the authorization signal may indicate that access criteria specified therein must be satisfied before generation of the authorization signal (such authorization signals do not provide conditional prescriptions, as the "conditions" are satisfied when the authorization signal is generated). In such embodiments, the authorization signals may not include any conditions at all, and instead may comprise data indicating what conditions have already been satisfied to justify access to a container 410.

In embodiments in which biosensor signals generated prior to an authorization signal may be utilized for satisfying access criteria, biosensor signals may be stored for a defined period of time to avoid having stale biosensor signals utilized to satisfy access criteria. As just one example, biosensor signals may be stored for 24-hours, for 12-hours, for 1-hour, and/or the like, such that old and irrelevant data cannot be utilized to satisfy access criteria. The biosensor data may be stored locally at a cradle 450, or may be stored via the management computing entity 20 in a profile (or EMR) associated with the user.

The biosensor data is generated as reflected in Block 903. As discussed herein, biosensors may be wearable devices utilized to monitor corresponding characteristics of a user. In other embodiments, the biosensors may comprise non-wearable sensors which may be utilized for periodic measurements of corresponding user characteristics. Such periodic measurements may be undertaken when the user elects to utilize the biosensor. As non-limiting examples, the biosensors may comprise body-temperature thermometers, pulse-measurement devices, blood-oxygen level measurement devices, pedometers, blood pressure measurement devices, and/or the like. The biosensors are configured to transmit corresponding biosensor signals to a processing entity. In certain embodiments, the biosensors are configured to transmit data wirelessly via a local area network, such as a Bluetooth-area network or other proximity-based communication protocol for communicating with a communications module of a cradle 450. In other embodiments, the biosensor may be configured for network communication (e.g., via Wi-Fi, via cellular networks, and/or the like), either directly or indirectly (e.g., through a cellular telephone), for communicating with the cradle 450, with the management computing entity 20, and/or the like. In certain embodiments, the biosensor signals may be transmitted together with metadata, such as data indicating the user identifier for which the biosensor signals are attributed. In other embodiments, the metadata may comprise a timestamp indicating when the biosensor signal is generated. In other embodiments, the metadata may comprise data indicating the identity of the biosensor itself, and the receiving processing entity (e.g., the cradle 450) may be configured to supplement the metadata with data indicating the user for which the biosensor signal is attributable and/or timestamp data indicative of when the biosensor signal is received.

As noted in Block 904, the biosensor data is received, and such data may be utilized to determine whether access criteria are satisfied for one or more containers 410, as reflected within Block 905. The access criteria is established as a part of the authorization signal, which identifies a target container (or container type; which may be identified by a specific unique container identifier or a container identifier that may be attributable to a plurality of containers of the same container type and having the same contents) and a user identifier for which the authorization signal is relevant. In certain embodiments, the authorization signal additionally identifies a cradle identifier to be utilized for providing the authorization signal, and which is associated with a cradle 450 to be utilized for executing the authorization signal and granting access to a particular container 410 in accordance with relevant conditions indicated within the authorization signal.

The conditions relevant for the authorization signal may be provided for consideration relative to other data that may be retrieved. For non-conditional prescriptions (or other non-conditional access to specified containers), the cradle 450 (or other processing resource) may cause the unlocking mechanism to unlock the specified container 410 upon confirming the user's identity and confirming the container's identity).

For conditional prescriptions, the cradle 450 (or other processing resource) collects/receives data relevant to the user and determines whether the received data satisfies applicable access criteria. In certain embodiments, the cradle 450 (or other processing resource) may generate an authorization profile associated with the authorization signal, such that data indicative of the access criteria may be stored together with relevant data attributable to the user, such as biosensor data, portions of EMR data (e.g., indicative of historical containers accessed by the user; indicative of a last access time for a particular container, and/or the like), and/or the like. Accordingly, the authorization profile may store data over time to determine if/when all access criteria relevant to a particular container 410 are satisfied, such that access to the container 410 may be granted to the user. In certain embodiments, a user profile may comprise additional contact data relevant to the user, such that the cradle 450 (or other processing resource) may be configured to generate and transmit an alert to the user informing the user when a particular container 410 is eligible to be opened. Such alerts may be provided as reminders to take a prescription medication, indications that the user's bodily characteristics satisfy criteria for access to a new prescription, and/or the like.

In other embodiments, the processing resource is configured to periodically check whether current biosensor signals (and/or other data relevant to the user) satisfy stored data indicative of access criteria. For example, such periodic checks may be performed upon a user placing a relevant container 410 onto a cradle 450, thereby requesting access to an interior thereof.

As just one example, the cradle 450 (or other processing resource) may determine whether identified biosensor-based criteria are satisfied for access to a particular container 410 by comparing received biosensor signals against biosensor-based criteria. As indicated at Block 908, the processing resource may then determine whether the biosensor signals satisfy applicable criteria before determining whether to generate a unlock signal (or otherwise activate the unlocking mechanism).

As another example, the cradle 450 (or other processing resource) may determine whether additional data stored in association with the user profile (e.g., within EMR data associated with the user profile) satisfies applicable historical access criteria. As a specific example, the historical access criteria may specify that the user must have accessed a first container 410 prior to accessing a second container 410. Thus, when the user requests access to the second container 410, the processing resource determines whether the user has previously accessed the first container 410. It should be understood that additional criteria may be implemented in such embodiments, such as implementing timing requirements indicating a minimum or maximum time period between accessing the first container 410 and the second container 410. As yet another example, historical access criteria may be utilized together with biosensor-based access criteria, such that access to a particular container 410 (a second container 410) may be conditioned upon previous access to a different container 410 (a first container 410) as well as satisfaction of one or more biosensor-based criteria. Such access criteria may be provided as a part of a prescribed treatment regimen, encompassing a series of objects, medications, diagnostic tests, and/or combinations thereof. Accordingly, a single authorization signal may provide conditions for access to a plurality of containers 410, to be accessed in a specified order as defined within the authorization signal. However, it should be understood that analogous sequential access criteria for a treatment regimen may be specified for a plurality of containers 410 with separate authorization signals corresponding to each container 410.

As a specific example, a physician may prescribe a sequential combination of at least one diagnostic test and at least one treatment for a particular medical condition, and such prescription may be based at least in part on one or more biosensor signals. Such a prescribed sequential combination of testing and treatment may be utilized, for example, in the testing and treatment for COVID-19. In such embodiments, the authorization signal may specify that access to a first container 410 containing a COVID-19 test kit may be provided to a user, and access criteria associated with the first container 410 includes signals that a user's body temperature exceeds a defined minimum threshold (indicating a fever) and the user's blood-oxygen level drops below a maximum threshold. Upon these criteria being satisfied, the user may be provided access to the interior of the first container 410 to access the COVID-19 test kit. The cradle 450 may then store historical access data indicating the user accessed the first container 410 and may provide this historical access data to the management computing entity 20 for storage in association with the user's profile (e.g., the user's EMR). The user may utilize the test kit and may send diagnostic samples to an appropriate lab, which may test the samples to ascertain whether the samples indicate the presence of the COVID-19 virus. The lab may then update the user's EMR (or other user profile) to reflect the test results.

Continuing the above-example, access to a second container 410 containing a COVID-19 treatment within the series of containers specified within the physician-specified authorization signal may be conditioned on the user's previous access to the first container 410 (as reflected within data stored within the user's profile), as well as stored data indicating a previous COVID-19 test indicated a positive test result, and biosensor data indicating a temperature above a minimum threshold and biosensor data indicating a blood-oxygen level below a maximum threshold. Upon detecting data within the user's profile indicating that the user has previously accessed the first container 410, that the user's previous COVID-19 test showed a positive test result, and upon receipt of biosensor signals satisfying applicable biosensor-based access criteria, the cradle 450 is configured to initialize the unlocking mechanism when the second container 410 is supported thereon, so as to grant the user access to COVID-19 treatment within the interior of the second container 410. In certain embodiments, such as those embodiments in which a treatment contained within the second container 410 comprises multiple time-spaced doses, a user may request access to the second container 410 multiple times, and subsequent access to the second container 410 may be conditioned upon the expiration of an applicable time criteria (e.g., a minimum time between doses), so as to ensure the user is taking the treatment medication at proper time intervals. As the user accesses the second container 410 for each dose, the cradle 450 records data indicating each access by the user (including metadata indicative of the time of access) for storage within and/or in association with the user's profile.

Because the historical access data may be stored in association with a user profile accessible to the management computing entity 20, access to containers 410 that is contingent on the user previously accessing a different container 410 having a specified container type (or container identifier) may be limited and controlled via a plurality of cradles 450. As just one example, access to a first container 410 may be granted via a first cradle 450 (e.g., a cradle at the user's home), and access to a second container 410 (access to which may be contingent on the user previously accessing the first container 410) may be granted via a second cradle 450 (e.g., a cradle 450 that is publicly accessible to users, for example, at a pharmacy providing contactless prescription access). To provide such access, the second cradle 450 may request data from the management computing entity 20 regarding the user (e.g., based on a received user identifier) to determine whether the user has satisfied applicable historical access criteria for a particular container 410. The management computing entity 20 may thus query the user's profile to determine whether the historical access criteria has been satisfied, and may transmit data to the second cradle 45 indicating whether the historical access criteria has been satisfied.

With reference again to FIG. 9, upon determining that all access criteria are satisfied for a particular container, the cradle 450 activates the unlocking mechanism as indicated in Block 909, causing the lock of the container 410 to be unlocked, thereby granting access to the interior of the container 410. As discussed herein, upon unlocking the container 410, the cradle 450 may simultaneously lock the container into contact with the cradle 450, such that the container 410 may not be removed from the cradle 450 while the container 410 is unlocked. Such locking between the container 410 and the cradle 450 may be actuated through independent locking mechanisms (e.g., magnetic, mechanical, and/or the like), or through a portion of the unlocking mechanism (e.g., a mechanical configuration, such as a pin that simultaneously unlocks a locking mechanism of the container 410 and prevents removal of the container 410 from the cradle 450).

As suggested herein, upon accessing a particular container 410 (e.g., detected based at least in part on initiation of the unlocking mechanism of the cradle 450), the cradle 450 may store data indicative of the user's access to the container (e.g., including a time of access, an identification of the container accessed (or the contents of the container accessed), and/or the like. Such data may be stored within and/or in association with a user profile (e.g., as a part of EMR data for the user), which may be later accessed as needed to satisfy applicable access criteria (e.g., time-based access criteria for the same container 410; historical access criteria for accessing a different container 410, and/or the like).

Moreover, the historical access data stored within and/or in association with a user profile, such as the data generated in response to a user accessing a particular container, may be utilized to monitor the quantity of objects (e.g., within a single container and/or within multiple containers). In certain embodiments, by monitoring the quantity of objects based at least in part on historical access data (e.g., data indicative of a number of times a particular container has been accessed and/or data indicative of a number of containers that have been accessed by a particular user), the management computing entity 20 may be configured to automatically generate an order to replenish objects within one or more containers.

In certain embodiments, monitoring the quantity of objects remaining accessible to the user (e.g., the objects may be accessible only in instances in which the user satisfies applicable access criteria, such as biometric-based access criteria, time based access criteria, and/or the like) may further comprise comparing the quantity of objects accessible to the user against a prescribed total quantity of objects that may be made available to the user without further intervention by a physician or other care provider, such that the management computing entity 20 may be configured to initiate an order to replenish objects only upon determining that initiating the order does not result in the user having access to more than the prescribed total quantity of objects. Moreover, the management computing entity 20 of certain embodiments may implement one or more timing models to determine an appropriate time to initiate an order to replenish one or more objects. As just one example, a timing model may be embodied as a machine-learning based timing model configured to determine a most-appropriate time to initial an order to replenish one or more objects based at least in part on a user's historical rate of usage of the one or more objects and/or based at least in part on an estimated shipping time to deliver the replenishing one or more objects to the user (within corresponding containers).

As a specific example, the one or more objects may comprise prescription pharmaceuticals, and a single container may contain a plurality of the pharmaceuticals, such that monitoring a number of times a user accesses the container may be utilized as a proxy for monitoring the number of the prescription pharmaceuticals taken by the user. The management computing entity 20 may store data indicative of an initial quantity of the prescription pharmaceuticals contained within the container, such that the number of prescription pharmaceuticals remaining within the container may be incrementally decreased with each detected time the user accesses the container (it should be understood that in certain embodiments, the management computing entity 20 may further store data indicative of a dose quantity, such that the quantity of prescription pharmaceuticals remaining within the container may be decreased by the dose quantity each time the user accesses the container). Once the total remaining quantity of the prescription pharmaceuticals within the container satisfies a replenishment criteria (e.g., a threshold quantity, a quantity determined based at least in part on execution of the timing model), the management computing entity 20 checks data stored in association with the user's profile (e.g., an EMR record associated with the user's profile) to retrieve data indicative of the number of permitted refills (instances of replenishment) for the prescription pharmaceutical, and upon determining that there is at least one additional permitted refill, the management computing entity 20 initiates an order to replenish the prescription pharmaceuticals for the user. As discussed herein, the prescription pharmaceuticals of the replenishment may be provided in a separate container having a corresponding container identifier and may be subject to access criteria analogous to the access criteria of the container housing the prior prescription pharmaceuticals.

V. Conclusion

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A computer-implemented method of unlocking a container, the method comprising:

receiving, via one or more processors, a container identifier provided from a container identification module associated with a locked container while the container is removably engaged with a cradle, wherein the cradle is configured to retrieve the container identifier from the container identification module and to transmit the container identifier via a network;

determining, based at least in part on the container identifier, one or more access criteria for the locked container;

receiving, via one or more processors, a provider authorization signal generated based at least in part on user input received via a provider user interface;

receiving, via the one or more processors, one or more biosensor signals generated at least in part by one or more biosensors associated with a user;

determining, via the one or more processors, whether one or more of the provider authorization signal and the one or more biosensor signals satisfy the one or more access criteria for the locked container; and upon determining the one or more access criteria for the locked container are satisfied:

transmitting a signal from the one or more processors to the cradle engaged with the locked container, wherein the cradle comprises an unlocking mechanism; and causing the unlocking mechanism of the cradle to unlock the locked container while the locked container is engaged with the cradle.

2. The method of claim 1, wherein at least one access criterion of the one or more access criteria comprises historical data of a first biosensor signal of the one or more biosensor signals satisfying one or more biosensor criteria.

3. The method of claim 1, wherein the one or more biosensor signals are generated at least in part by at least one of a temperature sensor or a blood oxygen sensor.

4. The method of claim 1, wherein the one or more biosensor signals comprise a first biosensor signal, and wherein the method further comprises:

receiving a second biosensor signal generated at least in part by a second biosensor; and wherein at least one access criterion of the one or more access criteria comprise the second biosensor signal satisfying one or more biosensor criteria.

5. The method of claim 1, wherein causing the unlocking mechanism of the cradle to unlock the locked container comprises causing the unlocking mechanism to generate an electromagnetic field that actuates a locking mechanism of the locked container to unlock the locked container.

6. The method of claim 1, wherein the container identification module comprises at least one of: a radio-frequency identification (RFID) reader, an optical sensor, or a color sensor.

7. The method of claim 1, further comprising:

receiving, via the one or more processors, historical access data associated with the user, wherein the historical access data indicates one or more objects historically accessed in association with the user; and determining whether the one or more access criteria are satisfied for the locked container further comprises determining whether the historical access data satisfies the one or more access criteria for the locked container.

8. The method of claim 1, further comprising:

upon generating a signal causing an unlocking mechanism to unlock the locked container, determine whether one or more replenishment criteria are satisfied for one or more objects identified as associated with the container identifier, and upon determining that the one or more replenishment criteria are satisfied, initiate an order for a new container housing one or more replenishment objects.

9. A system for unlocking a container, the system comprising:

one or more memory storage areas; and
one or more processors configured to:

receive a container identifier provided from a container identification module associated with a locked container while the container is removably engaged with a cradle, wherein the cradle is configured to retrieve the container identifier from the container identification module and to transmit the container identifier via a network;

determine, based at least in part on the container identifier, one or more access criteria for the locked container;

receive a provider authorization signal generated based at least in part on user input received via a provider user interface;

receive one or more biosensor signals generated at least in part by one or more biosensors associated with a user;

determine whether one or more of the provider authorization signal and the one or more biosensor signals satisfy the one or more access criteria for the locked container; and upon determining the one or more access criteria for the locked container are satisfied:

transmit a signal from the one or more processors to the cradle engaged with the locked container, wherein the cradle comprises an unlocking mechanism; and cause the unlocking mechanism of the cradle to unlock the locked container while the locked container is engaged with the cradle.

10. The system of claim 9, wherein at least one access criterion of the one or more access criteria comprises historical data of a first biosensor signal of the one or more biosensor signals satisfying one or more biosensor criteria.

11. The system of claim 9, wherein the one or more biosensor signals are generated at lest in part by at least one of a temperature sensor or a blood oxygen sensor.

12. The system of claim 9, wherein the one or more biosensor signals comprise a first biosensor signal, and wherein the one or more processors are further configured to:

receive a second biosensor signal generated at least in part by a second biosensor; and wherein at least one access criterion of the one or more access criteria comprises the second biosensor signal satisfying one or more biosensor criteria.

13. The system of claim 9, wherein causing the unlocking mechanism of the cradle to unlock the locked container comprises causing the unlocking mechanism to generate an electromagnetic field that actuates a locking mechanism of the locked container to unlock the locked container.

14. The system of claim 9, wherein the container identification module comprises at least one of: a radio-frequency identification (RFID) reader, an optical sensor, or a color sensor.

15. The system of claim 9, wherein the one or more processors are further configured to:

receive historical access data associated with the user, wherein the historical access data indicates one or more objects historically accessed in association with the user; and determining whether the one or more access criteria are satisfied for the locked container further comprises determining whether the historical access data satisfies the one or more access criteria for the locked container.

16. A computer program product for unlocking a container, the computer program product comprising at least one non-transitory computer-readable storage medium having computer-readable program code portions stored therein, the computer-readable program code portions configured to:

receive a container identifier provided from a container identification module associated with a locked container while the container is removably engaged with a cradle, wherein the cradle is configured to retrieve the container identifier from the container identification module and to transmit the container identifier via a network;

determine based at least in part on the container identifier, one or more access criteria for the locked container;

receive a provider authorization signal generated based at least in part on user input received via a provider user interface;

receive one or more biosensor signals generated at least in part by one or more biosensors associated with a user;

determine whether one or more of the provider authorization signal and the one or more biosensor signals satisfy the one or more access criteria for the locked container; and upon determining the one or more access criteria for the locked container are satisfied:
  transmit a signal from the one or more processors to the cradle engaged with the locked container, wherein the cradle comprises an unlocking mechanism; and
  cause the unlocking mechanism of the cradle to unlock the locked container while the locked container is engaged with the cradle.

17. The computer program product of claim 16, wherein the one or more biosensor signals are generated at least in part by at least one of a temperature sensor or a blood oxygen sensor.

18. The computer program product of claim 16, wherein the one or more biosensor signals comprise a first biosensor signal, and wherein the computer-readable program code portions are further configured to:
  receive a second biosensor signal generated at least in part by a second biosensor; and
  wherein at least one access criterion of the one or more access criteria comprises the second biosensor signal satisfying one or more biosensor criteria.

19. The computer program product of claim 16, wherein the computer-readable program code portions are furhter configured to:
  receive historical access data associated with the user, wherein the historical access data indicates one or more objects historically accessed in association with the user; and determine whether the one or more access criteria are satisfied for the locked container further comprises determining whether the historical access data satisfies the one or more access criteria for the locked container.

20. A system for unlocking a container, the system comprising:
  a cradle configured to accept a container thereon, wherein the cradle comprises:
    one or more engagement features configured to selectably engage a container while the container is placed on the cradle;
    a communication module configured to:
      receive container identification data from the container while the container is engaged with one or more engagement features;
      receive biosensor signals from one or more biosensors; and
      communicate data with a management computing entity;
    a processor configured to:
      determine access criteria for a container engaged with one or more engagement features on the cradle based at least in part on the container identification data and data received from the management computing entity; and
      based at least in part on the biosensor signals and data received from the management computing entity, generate an unlocking signal upon determining the access criteria are satisfied for the container; and
    an unlocking mechanism configured to, upon receipt of the unlocking signal from the processor, actuate a lock of the container engaged with one or more engagement features of the cradle.

21. The system of claim 20, wherein the access criteria comprise a historical access criterion specifying a user accessed a separate container prior to gaining access to the container, and wherein historical access data is received from the management computing entity.

* * * * *

UNITED STATES PATENT AND TRADEMARK OFFICE
CERTIFICATE OF CORRECTION

PATENT NO. : 11,600,121 B2
APPLICATION NO. : 17/083760
DATED : March 7, 2023
INVENTOR(S) : Jennie Audrey Ehlert et al.

It is certified that error appears in the above-identified patent and that said Letters Patent is hereby corrected as shown below:

In the Claims

In Column 31, Line 31, Claim 4, delete "comprise" and insert -- comprises --, therefor.

In Column 32, Line 31, Claim 11, delete "at lest" and insert -- at least --, therefor.

In Column 33, Line 37, Claim 19, delete "furhter" and insert -- further --, therefor.

Signed and Sealed this
Sixteenth Day of May, 2023

Katherine Kelly Vidal
*Director of the United States Patent and Trademark Office*